(12) United States Patent
Bardotti

(10) Patent No.: US 8,790,893 B2
(45) Date of Patent: Jul. 29, 2014

(54) MEASURING DEGREE OF POLYMERISATION FOR MENINGOCOCCAL CAPSULAR SACCHARIDES THAT CONTAIN SIALIC ACID

(75) Inventor: Angela Bardotti, Siena (IT)

(73) Assignee: Novartis AG, Basel (CH)

( * ) Notice: Subject to any disclaimer, the term of this patent is extended or adjusted under 35 U.S.C. 154(b) by 999 days.

(21) Appl. No.: 12/875,967

(22) Filed: Sep. 3, 2010

(65) Prior Publication Data

US 2011/0159029 A1  Jun. 30, 2011

Related U.S. Application Data

(62) Division of application No. 11/597,451, filed as application No. PCT/IB2005/002264 on May 23, 2005, now Pat. No. 7,803,583.

(30) Foreign Application Priority Data

May 21, 2004 (GB) .................................. 0411387.4

(51) Int. Cl.
*C12P 1/00* (2006.01)
*C12N 9/00* (2006.01)

(52) U.S. Cl.
USPC ........................................... 435/41; 435/183

(58) Field of Classification Search
None
See application file for complete search history.

(56) References Cited

U.S. PATENT DOCUMENTS

2003/0219830 A1  11/2003  Venkataraman et al.

FOREIGN PATENT DOCUMENTS

| EP | 0462794 | 12/1991 |
|---|---|---|
| WO | WO-03/007985 | 1/2003 |
| WO | WO-03/080678 | 10/2003 |

OTHER PUBLICATIONS

Ashwell et al (1994), *Analytical Biochemistry* 222:495-502.
Bardotti, A. et al, (2005) *Vaccine* 23(16):1887-1899.
Ravenscroft, N. et al, (1999) *Vaccine* 17(22):2802-2816.
Vimr, E. et al, (1984) *PNAS USA* 81(7):1971-1975.
Costantino, P. et al., "Size fractionation of bacterial capsular polysaccharides for their use in conjugete vaccines" Vaccine 17:1251-1263 (1999).
Jodar, L. et al., "Scientific challenges for the quality control and production of group C meningococcal conjugate vaccines," Vaccine 22:1047-1033 (2004).
von Hunolstein, C. et al., "Simple and rapid technique for monitoring the quality of meningococcal polysaccharides by high perofrmance size exclusion chromatography, "J. Biochem. Biophys. Methods 50:201-290 (2003).

*Primary Examiner* — Albert Navarro
(74) *Attorney, Agent, or Firm* — Helen Lee; Otis Littlefield

(57) ABSTRACT

The degree of polymerisation (DP) is an important parameter for analysis of saccharide antigens, particularly in glycoconjugates. The invention provides methods that can be used to measure DP for capsular saccharides, particularly for meningococcal saccharides e.g. from serogroups W135 and Y. A preferred method is based on reduction of terminal sialic acid residues on saccharides, with DP then being calculated by comparing the molar ratio of total sialic acid to reduced sialic acid.

19 Claims, 24 Drawing Sheets

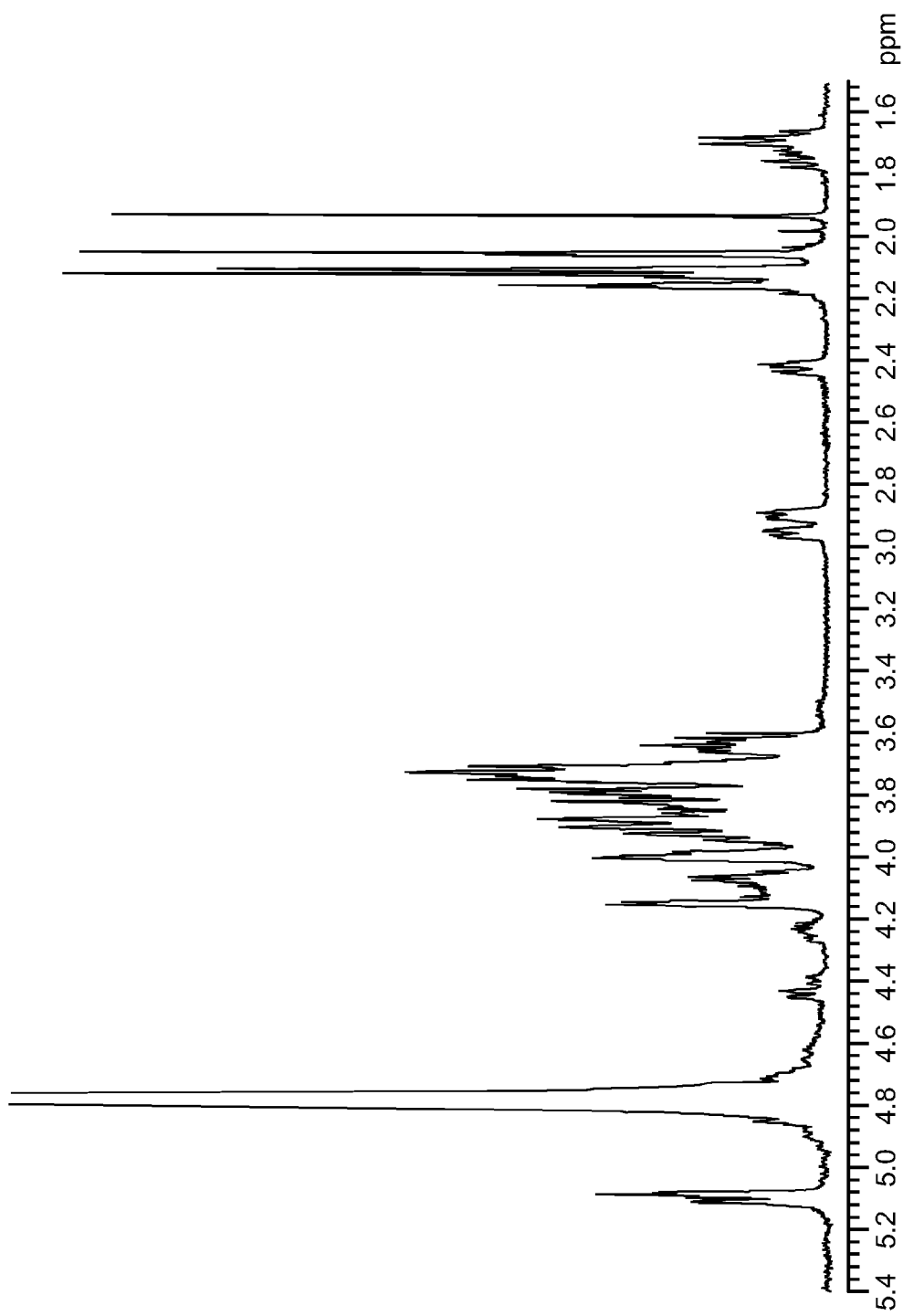

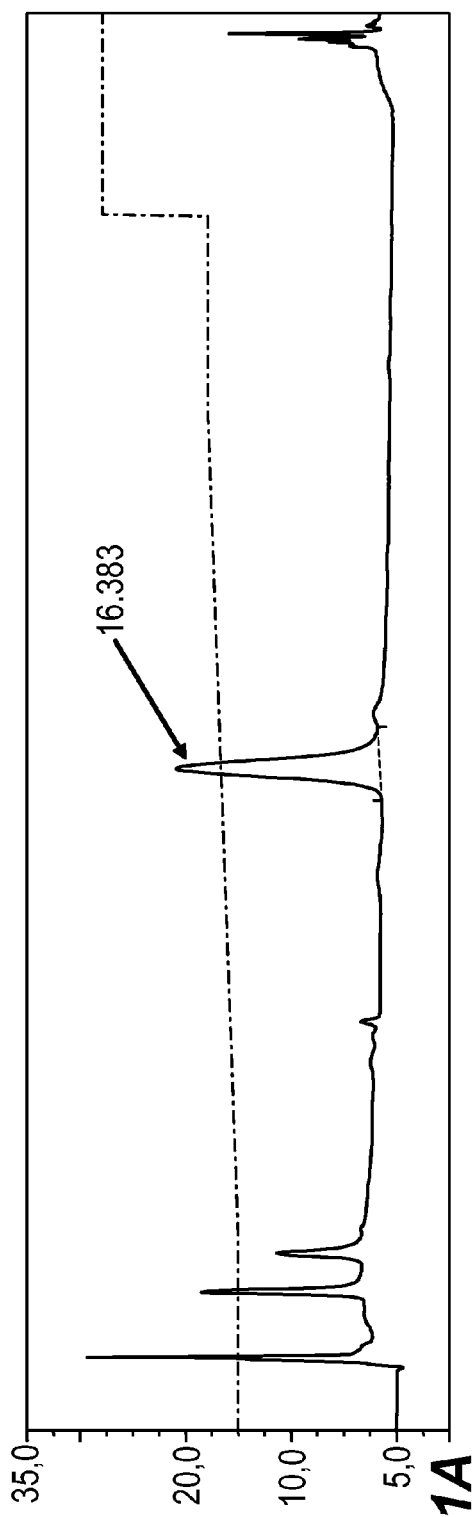
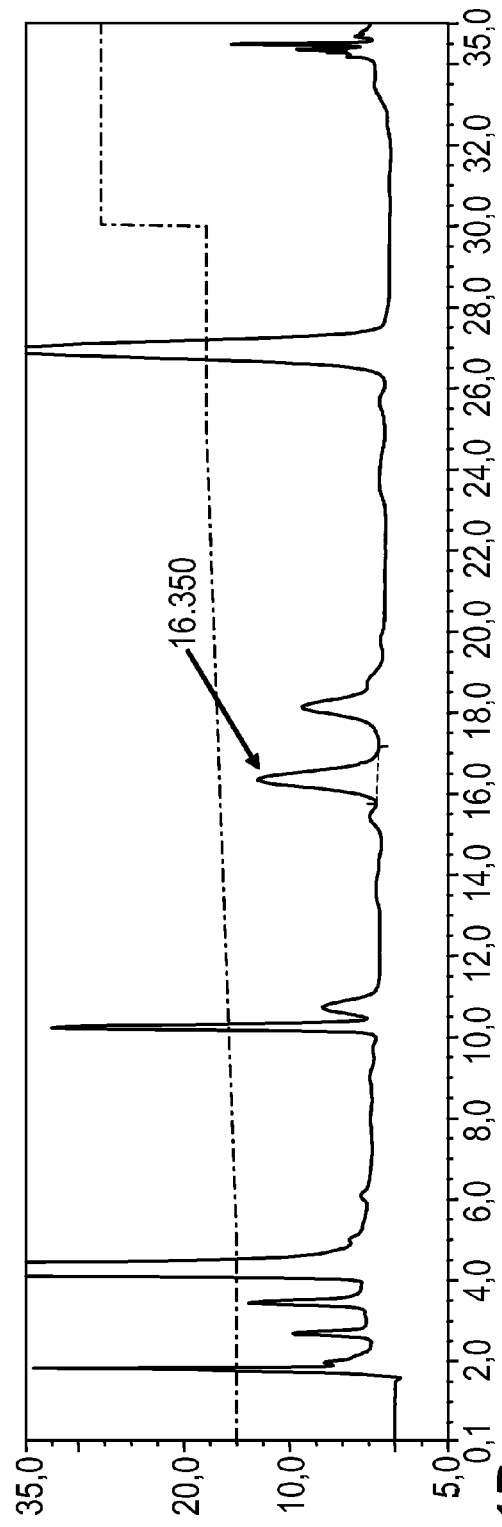
FIG. 21A
FIG. 21B

MEASURING DEGREE OF POLYMERISATION FOR MENINGOCOCCAL CAPSULAR SACCHARIDES THAT CONTAIN SIALIC ACID

CROSS REFERENCE TO RELATED APPLICATIONS

This application is a divisional application of U.S. Ser. No. 11/597,451, which is the National Stage of International Application No. PCT/IB2005/02264, filed May 23, 2005, which claims the benefit of GB Application Ser. No. 0411387.4, filed May 21, 2004, each of which is hereby incorporated by reference in its entirety.

All documents cited herein are incorporated by reference in their entirety.

TECHNICAL FIELD

This invention is in the field of analysis and quality control of vaccines that include bacterial capsular saccharides, and in particular those where the saccharides are conjugated to a carrier.

BACKGROUND ART

Immunogens comprising capsular saccharide antigens conjugated to carrier proteins are well known in the art. Conjugation converts T-independent antigens into T-dependent antigens, thereby enhancing memory responses and allowing protective immunity to develop, and the prototype conjugate vaccine was for *Haemophilus influenzae* type b (Hib) [e.g see chapter 14 of ref. 1]. Since the Hib vaccine, conjugated saccharide vaccines for protecting against *Neisseria meningitidis* (meningococcus) and against *Streptococcus pneumoniae* (pneumococcus) have been developed. Other organisms where conjugate vaccines are of interest are *Streptococcus agalactiae* (group B *streptococcus*) [2], *Pseudomonas aeruginosa* [3] and *Staphylococcus aureus* [4].

Rather than use full-length capsular saccharides, it is possible to select oligosaccharide fragments of desired size after a hydrolysis step [e.g. ref. 5], and it has been reported that conjugates made with intermediate chain-length oligosaccharides offer improved immunogenicity [e.g. refs. 6 & 7]. Of the three *N. meningitidis* serogroup C conjugated vaccines that have been approved for human use, Menjugate™ [8] and Meningitec™ are based on oligosaccharides, whereas NeisVac-C™ uses full-length polysaccharide. Measurement of oligosaccharide length (e.g. by measuring the degree of polymerisation, or 'DP' i.e. the number of repeating units in the chain) can therefore be used for indirect assessment of immunogenicity.

Where oligosaccharide fragments are included in a vaccine, quality control for manufacturing and release requires that oligosaccharides have a defined length, and that this length is consistent between batches. Thus DP is also useful in quality control, and the European Directorate for Quality of Medicines (EDQM) has an Official Control Authority Batch Release (OCABR) for conjugated Hib vaccines that specifically requires submission of data relating to DP and molecular size distribution of saccharides used during manufacture. DP can also be used for monitoring vaccine stability. Saccharide antigens can readily depolymerise at ambient temperatures [9,10], causing a decrease in immunogenicity and an increase in vaccine heterogeneity. Such changes can be monitored by following DP over time during storage.

Average DP in an oligosaccharide pool can be measured using a number of methodologies, and in some cases the choice of method will depend on the saccharide under analysis. Techniques such as colorimetric and/or enzymatic analysis have been described for oligosaccharides from Hib and from serogroups A and C of meningococcus [5,11,12], but the inventors have found that the glycosidic linkages in the saccharides of meningococcal serogroups W135 and Y ('MenW135' and 'MenY') mean that these techniques cannot be used.

Although methods for measuring DP of MenA and MenC saccharides for conjugate vaccines have previously been described [e.g. refs. 5 & 13], there remains a need for methods that can be applied to the saccharides of serogroups W135 and Y. It is thus an object of the invention to provide improvements in methods for DP assessment of saccharides, and in particular to provide methods that can be used to measure DP for saccharides from meningococcal serogroups W135 and Y.

DISCLOSURE OF THE INVENTION

The inventors have discovered a method that can be used to measure DP for the capsular saccharides of meningococcal serogroups W135 and Y. Thus the invention provides a process for measuring the degree of polymerisation of a capsular saccharide, characterised in that the saccharide is from meningococcal serogroup W135 or serogroup Y. The method is conveniently performed by including a step of chromatographic separation. In a composition comprising a population of different-sized capsular saccharides, the invention provides a process for measuring average DP.

The process typically involves hydrolysis of the saccharides to release constituent monosaccharides, with analysis being based on the monosaccharides. Thus the invention provides a process for measuring the degree of polymerisation of a capsular saccharide from meningococcal serogroup W135 or serogroup Y, wherein the process comprises the steps of: (i) hydrolysing the saccharide to give a saccharide hydrolysate containing monosaccharide subunits; (ii) quantifying the monosaccharide subunits in the hydrolysate, wherein the quantitative results of step (ii) are used to calculate the degree of polymerisation.

Prior to hydrolysis, the process typically involves chemical modification of a terminal residue (either at the reducing terminus or the non-reducing terminus) of the saccharide such that, after hydrolysis to monosaccharides, the terminal residue can be distinguished from non-terminal residues. Thus the invention provides a process for measuring the degree of polymerisation of a capsular saccharide from meningococcal serogroup W135 or serogroup Y, wherein the process comprises the steps of: (i) modifying a terminal monosaccharide subunit of the saccharide, to give a modified terminal monosaccharide; (ii) hydrolysing the saccharide to give a saccharide hydrolysate containing monosaccharide subunits, including the modified terminal monosaccharide; (iii) quantifying the monosaccharide subunits from the hydrolysate; (iv) quantifying the modified terminal monosaccharide from the hydrolysate; and (v) using the quantitative results of steps (iii) and (iv) to calculate the degree of polymerisation.

The method is applicable more generally to any saccharide that contains more than one different type of monosaccharide subunit and includes a terminal sialic acid residue. Advantageously, the method provides DP information based only on quantification of the sialic acid residues in a saccharide, without requiring analysis of any other type of monosaccharide. Thus the invention provides a process for measuring the degree of polymerisation of a capsular saccharide, wherein: (a) the saccharide comprises sialic acid monosaccharide subunits and non-sialic acid monosaccharide subunits; (b) the saccharide has a terminal sialic acid monosaccharide subunit; and (c) the process comprises the steps of (i) modifying a terminal sialic acid subunit of the saccharide, to give a modified terminal sialic acid subunit; (ii) hydrolysing the saccharide to give a saccharide hydrolysate containing sialic acid subunits, including modified terminal sialic acid subunits; (iii) quantifying the sialic acid subunits from the hydrolysate, including the modified terminal sialic acid subunits; and (iv) using the quantitative results of step (iii) to calculate the degree of polymerisation.

A preferred method of the invention is based on reduction of terminal sialic acid residues on saccharides, with DP then being calculated by comparing the molar ratio of total sialic acid to reduced sialic acid. The invention thus provides a process for measuring the degree of polymerisation of a capsular saccharide, wherein: (a) the saccharide comprises sialic acid monosaccharide subunits and non-sialic acid monosaccharide subunits; (b) the saccharide has a terminal sialic acid monosaccharide subunit; and (c) the process comprises the steps of: (i) reducing the terminal sialic acid monosaccharide subunit to give a reduced sialic acid monosaccharide subunit; (ii) hydrolysing the saccharide to give a hydrolysate containing monosaccharide subunits; (iii) determining the ratio of total (i.e. reduced and non-reduced) sialic acid to reduced sialic acid in the hydrolysate.

In terms of a composition comprising a population of different-sized capsular saccharides, the invention provides a process for measuring the average degree of polymerisation of the saccharides, wherein: (a) the saccharides comprise sialic acid monosaccharide subunits and non-sialic acid monosaccharide subunits; (b) the saccharides have terminal sialic acid monosaccharide subunits; and (c) the process comprises the steps of: (i) reducing the terminal sialic acid monosaccharide subunits to give reduced sialic acid monosaccharide subunits; (ii) hydrolysing the saccharides to give a saccharide hydrolysate containing monosaccharide subunits; (iii) determining the ratio of total (i.e. reduced and non-reduced) sialic acid to reduced sialic acid in the hydrolysate. The composition may include saccharides that do not have terminal sialic acid monosaccharide subunits.

A method for analysing the length and composition of poly-sialic acid saccharides has been described [14] in which terminal residues are oxidised and/or reduced, after which the saccharide is digested with neuraminidase enzyme to release its sialic acid monosaccharide subunits. However, this prior art process was described only for saccharides composed solely of sialic acids (including N-acetyl-neuraminic acid, N-glycolyl-neuraminic acid and deaminated sialic acid) and was technically limited to saccharides that can be enzymatically cleaved into monosaccharides. In contrast, the method of the invention can deal with saccharides that include non-sialic acid monosaccharides, and does not require (but does not exclude) the use of enzymatic hydrolysis.

The inventors have also discovered a method that can be used to measure DP for the capsular saccharides of meningococcal serogroup C. The method is again based on reduction of terminal sialic acid residues, with DP being calculated in the same way. The method is applicable more generally to any saccharide that contains sialic acid residues that are linked $\alpha$ 2→9. Preferably, the method does not involve enzymatic depolymerisation. The invention thus provides a process for measuring the degree of polymerisation of a capsular saccharide, wherein: (a) the saccharide comprises sialic acid monosaccharide subunits that are linked $\alpha$ 2→9; (b) the saccharide has a terminal sialic acid monosaccharide subunit; and (c) the process comprises the steps of: (i) reducing the terminal sialic acid monosaccharide subunit to give a reduced sialic acid monosaccharide subunit; (ii) hydrolysing the saccharide to give a hydrolysate containing monosaccharide subunits; (iii) determining the ratio of total (i.e. reduced and non-reduced) sialic acid to reduced sialic acid in the hydrolysate.

In terms of a composition comprising a population of different-sized capsular saccharides, the invention provides a process for measuring the average degree of polymerisation of the saccharides, wherein: (a) the saccharide comprises sialic acid monosaccharide subunits that are linked $\alpha$ 2→9; (b) the saccharides have terminal sialic acid monosaccharide subunits; and (c) the process comprises the steps of: (i) reducing the terminal sialic acid monosaccharide subunits to give reduced sialic acid monosaccharide subunits; (ii) hydrolysing the saccharides to give a hydrolysate containing monosaccharide subunits; (iii) determining the ratio of total (i.e. reduced and non-reduced) sialic acid to reduced sialic acid in the hydrolysate.

A method for analysing the length and composition of poly-sialic acid saccharides has been described [14] in which terminal residues are oxidised and/or reduced, after which the saccharide is digested with neuraminidase enzyme to release its sialic acid monosaccharide subunits. However, this prior art process was described only for saccharides composed of $\alpha$ 2→8 linked sialic acids and was technically limited to saccharides that can be enzymatically cleaved into monosaccharides. In contrast, the method of the invention is concerned with $\alpha$ 2→9 linked sialic acids, and preferably utilises non-enzymatic hydrolysis, typically chemical (e.g. acidic) hydrolysis.

A method for determining the length of a serogroup C saccharide is known [5] where DP was determined by comparing the ratio between total sialic acid and formaldehyde generated by periodate treatment of the MenC saccharide. This prior art method involves modification at the non-reducing terminus of the polymer, and does not involve the generation of sialitol.

Capsular Saccharides Containing Sialic Acid Residues and Non-sialic Acid Residues In some embodiments, the invention provides methods for analysing saccharides that comprise both sialic acid monosaccharide subunits and non-sialic acid monosaccharide subunits. More particularly, the saccharides are preferably made up of repeating units, and the repeating units consist of sialic acid monosaccharide subunits and non-sialic acid monosaccharide subunits.

Two particular saccharides of interest are the capsular saccharides of *Neisseria meningitidis* serogroups W135 and Y. The saccharides naturally have a sialic acid residue at their reducing end and either glucose or galactose at the non-reducing end. The sialic acid in the native saccharides of these serogroups is N-acetyl neuraminic acid, or 'NeuNAc'.

The serogroup W135 saccharide is a polymer consisting of sialic acid-galactose disaccharide units. It has variable O-acetylation at the 7 and 9 positions of the sialic acid [15]. The structure is shown in FIG. 1 and is written as: →4)-D-Neup5Ac(7/9OAc)-$\alpha$-(2→6)-D-Gal-$\alpha$-(1→

The serogroup Y saccharide is similar to the serogroup W135 saccharide, except that the disaccharide repeating unit includes glucose instead of galactose (see FIG. 3). It has variable O-acetylation at the 7 and 9 positions of the sialic acid [15]. The serogroup Y structure is shown in FIG. 2 and is written as: →4)-D-Neup5Ac(7/9OAc)-$\alpha$-(2→6)-D-Glc-$\alpha$-(1→

In other embodiments, the invention provides methods for analysing saccharides that comprise (α 2→9)-linked sialic acids. The serogroup C capsular saccharide is a homopolymer of (α 2→9) linked sialic acid, with variable O-acetylation at positions 7 and/or 8.

The capsules of serogroups C, W135 and Y differ from serogroup A, which has a homopolymer of (α1→6)-linked N-acetyl-D-mannosamine-1-phosphate, and from serogroup B, which has a homopolymer of (α 2→8)-linked sialic acid.

Degree of Polymerisation

The degree of polymerisation of a saccharide is defined as the number of repeating units in that saccharide. For a homopolymer, the degree of polymerisation is thus the same as the number of monosaccharide units. For a heteropolymer, however, the degree of polymerisation is the number of monosaccharide units in the whole chain divided by the number of monosaccharide units in the minimum repeating unit e.g. the DP of $(Glc\text{-}Gal)_{10}$ is 10 rather than 20, and the DP of $(Glc\text{-}Gal\text{-}Neu)_{10}$ is 10 rather than 30.

Within a mixture of saccharides having the same basic repeating structure but different lengths (e.g. in a partial hydrolysate of a long polysaccharide) then it is normal to measure the average DP of a population rather than to measure the DP of individual molecules. If the size range is too large, such that an average value will not be meaningful, then it is possible to measure DP for individual fractions of a mixture after separation (e.g. after separation by size). In general, the invention will be used to measure the average DP of compositions containing mixed-length saccharides.

Reduction of the Terminal Sialic Acid Monosaccharide Subunit

The invention is used to analyse saccharides that have terminal sialic acid residues. In particular, it is used to analyse saccharides that have sialic acid residues at the reducing terminus.

Any suitable chemistry can be used for reduction of the terminal sialic acid residue, generally involving incubating the saccharide with a reducing agent. Suitable conditions for any given reducing agent and any given saccharide can be determined by routine analysis.

A preferred reducing agent is sodium borohydride ($NaBH_4$), which reduces terminal sialic acid residues [14] under alkaline conditions. The product of this reduction is sometimes referred to as sialitol [16]. Incubation with $NaBH_4$ for 2 hours at 37° C. is generally adequate. After reduction in alkaline conditions then a composition is preferably neutralised e.g. by adding mildly-acidic ammonium acetate.

Hydrolysing the Saccharide to Give a Saccharide Hydrolysate

After reduction of the terminal sialic acid residue, the saccharide is broken into its constituent monosaccharide units. In general terms, depolymerisation of saccharides to yield monosaccharides can be performed chemically or enzymatically. If there is no enzyme for performing a given cleavage reaction, however, then the chemical route must be used.

Chemical hydrolysis of saccharides generally involves treatment with either acid or base under conditions that are standard in the art. Conditions for depolymerisation of capsular saccharides to their constituent monosaccharides are known in the art. For serogroup W135 and Y saccharides, acid hydrolysis is preferred. Acid hydrolysis using TFA (trifluoroacetic acid) can be used for hydrolysis of all of serogroups C, W135 and Y, with a slightly lower incubation temperature being preferred for serogroup C to avoid degradation of its sialic acids (90° C. rather than 100° C.). A typical TFA treatment involves addition of TFA to a final concentration of 2 M, followed by heating to 90-100° C. for 90 minutes. The serogroup C saccharide can be hydrolysed for total saccharide content analysis by treatment with 100 mM HCl at 80° C. for 2 hours [17]. Other typical hydrolysis conditions involve millimolar concentrations of a weak acid (e.g. acetic acid) at elevated temperatures (e.g. 70-80° C.).

Enzymes are available for cleaving the α 2→9 linkages found in serogroup C, and these may be used with the invention. However, enzymes generally require the saccharides to be de-O-acetylated prior to hydrolysis, so if it is desired to maintain O-acetylation [15] then it is preferred to hydrolyse the saccharide chemically. Chemical hydrolysis may also be preferred where enzymatic hydrolysis proceeds slowly. Enzymes for cleaving serogroups W135 and Y are not generally available.

Although the invention has been defined above in terms of preparing and analysing a hydrolysate containing monosaccharide subunits, the invention can also be applied to hydrolysates containing disaccharide, trisaccharide, tetrasaccharide etc. fragments of the capsular saccharide, but it is easier to prepare a hydrolysate of monosaccharides. Hydrolysis conditions that provide a homogenous population of di-, tri-, tetra- etc. saccharides, such that there is only a single compound to be quantified, are much more difficult to control than simply allowing depolymerisation to proceed to completion i.e. to give monosaccharides.

After depolymerisation, saccharide hydrolysates may be dried e.g. using a vacuum drier.

Determining the Ratio of Total Sialic Acid to Reduced Sialic Acid

Hydrolysis gives a saccharide hydrolysate that contains the monosaccharide subunits of the original saccharide. In embodiments where saccharides comprise both sialic acid subunits and non-sialic acid subunits, the hydrolysate will contain sialic acid and non-sialic acid monosaccharides; in embodiments where saccharides are sialic acid homopolymer then the hydrolysate will contain only sialic acids; in both cases, a fraction of the sialic acid monosaccharides will be in a modified form (e.g. a reduced form). That fraction can be used to determine the DP of the original saccharide. For example, if one in ten of the sialic acid residues in the mixture is a modified residue and the minimum repeating unit of the saccharide contains a single sialic acid residue then the original saccharide has a DP of 10.

Quantities of individual monosaccharides can be determined in terms of numbers (e.g. moles) of molecules, masses, ratios or concentrations. It is typical to work in moles in order to simplify the calculation of ratios, particularly where constituent monosaccharides have different molecular masses, but any of these measures can be used and interchanged to determine monosaccharide content of the mixtures. For quantitative measurement, analytical results may be compared to a standard with a known content of a particular saccharide.

The depolymerised mixture is preferably hydrolysed completely to monosaccharides. The inventors have found that incomplete hydrolysis sometimes occurs, giving mixtures in which disaccharide fragments are present (i.e. Gal-NeuNAc for MenW135, and Glc-NeuNAc for MenY). For instance, treatment of MenW135 or MenY saccharides with 2M TFA at 90° C. has been seen to give a mixture of monosaccharides and disaccharides, whereas increasing the hydrolysis temperature to 100° C. gives substantially only monosaccharides. Incomplete hydrolysis even at 90° C. was not expected but, now that it has been observed, the skilled person can, if necessary, modify any particular hydrolysis method to ensure total hydrolysis e.g. by increasing temperature, etc.

Methods for quantifying sialic acid monosaccharides are well known in the art. Methods may be direct or indirect (e.g.

they may involve derivatisation of the monosaccharides followed by an analysis that correlates with original monosaccharide content). Preferred methods can analyse sialic acid in the presence of other monosaccharides, such that they do not need to be separated from each other before analysis. In addition, methods may be used for conjugated saccharides in which, after deconjugation, the carrier and the saccharide need not be separated. One such method is anion chromatography, and in particular high performance anion exchange chromatography (HPAEC), usually with pulsed amperometric detection (PAD) [18,19]. HPAEC-PAD systems are provided by Dionex™ Corporation (Sunnyvale, Calif.) e.g. the BioLC™ system, using a column such as PA1 [10 μm diameter polystyrene substrate 2% crosslinked with divinylbenzene, agglomerated with 500 nm MicroBead quaternary ammonium functionalized latex (5% crosslinked)] or PA10 [10 μm diameter ethylvinylbenzene substrate 55% crosslinked with divinylbenzene, agglomerated with 460 nm MicroBead difunctional quaternary ammonium ion (5% crosslinked)]. These systems can quantitatively analyse individual saccharides within mixtures without the need for derivatisation or pre-analysis separation. For saccharide analysis, it may be desired to filter other compounds before entry to the column, and Dionex™ produce pre-column traps and guards for this purpose e.g. an amino trap for removing amino acids, a borate trap, etc.

An alternative method for quantifying sialic acid monosaccharides within a depolymerised mixture is nuclear magnetic resonance (NMR). For ease of use and for high sensitivity, however, the chromatographic methods of the invention are preferred. Whichever method is chosen, however, in some embodiments of the invention it is important that reduced sialic acid can be distinguished from non-reduced sialic acid. This may involve unique signals from each, or may involve one unique signal and one combined signal, with the difference between the two giving signals providing the necessary information.

Another method for quantifying sialic acid monosaccharides is by colorimetric assay [80]. This method is particularly useful for quantifying non-reduced sialic acid after acid hydrolysis in TFA.

Once the relative quantities of modified and non-modified (e.g. reduced and non-reduced) sialic acid have been determined then it is simple to establish the DP of the original saccharide.

In addition to quantifying sialic acids in the hydrolysate, methods of the invention may involve quantification of other monosaccharides (e.g. of glucose or galactose) which may be derived from the same saccharide as the sialic acids, or from other saccharides. These measurements can be used for determining parameters other than DP, or can be used as part of the DP determination e.g. as confirmation or in place of measurement of total sialic acid, particularly where the molar quantities of sialic acid and the other monosaccharide are the same, as in the W135 and Y saccharides.

The process of the invention is typically destructive. Rather than perform the process on a complete composition, therefore, it is more typical to take a sample from a composition of interest and then perform the analysis on the sample.

Conjugates

The invention is useful for analysing saccharide content of vaccines, and in particular for vaccines that comprise a conjugated saccharide. Covalent conjugation is used to enhance immunogenicity of saccharides by converting them from T-independent antigens to T-dependent antigens, thus allowing priming for immunological memory. Conjugation is particularly useful for paediatric vaccines and is a well known technique [e.g. reviewed in refs. 20 to 29]. Saccharides may be linked to carriers directly [30, 31], but a linker or spacer is generally used e.g. adipic acid, β-propionamido [32], nitrophenyl-ethylamine [33], haloacyl halides [34], glycosidic linkages [35], 6-aminocaproic acid [36], ADH [37], $C_4$ to $C_{12}$ moieties [38], etc.

Typical carrier proteins in conjugates are bacterial toxins or toxoids, such as diphtheria toxoid or tetanus toxoid. The $CRM_{197}$ diphtheria toxin derivative [39-41] is the carrier protein in Menjugate™ and Meningitec™, whereas tetanus toxoid is used in NeisVac™. Diphtheria toxoid is used as the carrier in Menactra™. Other known carrier proteins include the *N. meningitidis* outer membrane protein [42], synthetic peptides [43,44], heat shock proteins [45,46], pertussis proteins [47,48], cytokines [49], lymphokines [49], hormones [49], growth factors [49], artificial proteins comprising multiple human $CD4^+$ T cell epitopes from various pathogen-derived antigens [50], protein D from *H. influenzae* [51,52], pneumococcal surface protein PspA [53], iron-uptake proteins [54], toxin A or B from *C. difficile* [55], etc. Compositions may use more than one carrier protein e.g. to reduce the risk of carrier suppression, and a single carrier protein might carry more than one saccharide antigen [56]. Conjugates generally have a saccharide:protein ratio (w/w) of between 1:5 (i.e. excess protein) and 5:1 (i.e. excess saccharide). Compositions may include free carrier protein in addition to the conjugates [57].

The invention is particularly useful prior to conjugation at the stage where it is necessary to ensure that the correctly-sized saccharide chains are selected for production of the conjugate.

The invention allows the progress of fragmentation of a full-length polysaccharide prior to conjugation to be checked or monitored. Where oligosaccharides of a particular length (or range of lengths) is desired then it is important that fragmentation of the polysaccharide should not be so extensive as to take depolymerisation past the desired point (e.g. at the extreme, to give monosaccharides). The invention allows the progress of this partial depolymerisation to be monitored, by measuring average chain length over time. Thus the invention provides a process for measuring the degree of polymerisation of saccharide(s) in a composition, comprising the steps of: (a) starting depolymerisation of the saccharide(s) in the composition; and, (b) at one or more time points thereafter, measuring DP of the saccharide(s) as described above. In an initial run of experiments then it will be usual to measure DP at several time points in order to determine progress over time, but after standard conditions have been established then it be usual to measure DP at a set time point for confirmatory purposes. Once DP is at a desired level then the process may comprise the further step of: (c) stopping the depolymerisation, e.g. by washing, separating, cooling, etc. The process may also comprise the further step of conjugation of the depolymerised saccharide to a carrier protein, after optional chemical activation.

The invention also allows selection of oligosaccharide chains of a desired length after fragmentation. Thus the invention provides a process for selecting saccharides for use in preparing a glycoconjugate, comprising the steps of: (a) obtaining a composition comprising a mixture of different polysaccharide fragments having different degrees of polymerisation; (b) separating the mixture into sub-mixtures; (c) determining the DP of one or more sub-mixtures using a process as described above; and (d) using the results of step (c) to select one or more sub-mixtures for use in conjugation. The process may involve fragmentation of the polysaccharide prior to step (a), or may start with an already-prepared mixture. The fragments may be fragments of the same polysaccharide e.g. of the same serogroup. After step (d), the process may comprise the step of conjugation to a carrier protein, after optional chemical activation.

Prior to conjugation it is usual for a saccharide to be chemically activated in order to introduce a functional group that can react with the carrier. Conditions for saccharide activation can cause hydrolysis, and so it is useful to check DP after activation. The term "saccharide" should, where appropriate, be taken to include these activated saccharides. Moreover, the invention provides a process for preparing an activated saccharide for use in preparing a glycoconjugate, comprising the steps of: (a) obtaining a saccharide; (b) chemically activating the saccharide to introduce a functional group that can react with a carrier protein; and (c) measuring the DP of the product of step (b) as described above. The process may include the further step of: (d) reacting the activated saccharide with the carrier protein (which may itself have been activated) to give the glycoconjugate. The process may involve fragmentation of a polysaccharide prior to step (a), or may start with an already-prepared mixture.

The invention can also be used after conjugation. After conjugation, compositions can be analysed using the invention in three ways: first, the DP of total saccharides in a composition can be measured e.g. prior to mixing of different conjugates, or prior to release of a vaccine (for regulatory or quality control purposes); second, the DP of free unconjugated saccharide in a composition can be measured e.g. to check for incomplete conjugation, or to follow conjugate hydrolysis by monitoring increasing free saccharide over time; third, the DP of conjugated saccharide in a composition can be measured, for the same reasons. The first and third ways require the saccharide to be released from the conjugate prior to analysis. In situations where conjugation of the saccharide involved reaction or modification of the sialic acid residue its reducing end, however, such that the residue is no longer amenable to reduction, then the invention can be used only for saccharides where a terminal sialic acid can be re-generated (or where a reduced terminal sialic acid can be generated directly).

To separately assess conjugated and unconjugated saccharides, they must be separated. Free (i.e. unconjugated) saccharide in an aqueous composition can be separated from conjugated saccharide in various ways. The conjugation reaction changes carious chemical and physical parameters for the saccharide, and the differences can be exploited for separation. For example, size separation can be used to separate free and conjugated saccharide, as the conjugated material has a higher mass due to the carrier protein. Ultrafiltration is a preferred size separation method. As a further alternative, if conjugates have been adsorbed to an adjuvant then centrifugation will separate adsorbed conjugate (pellet) from free saccharide (supernatant) that desorbs after hydrolysis.

The invention provides a method for analysing a glycoconjugate, comprising the steps of: (a) treating the glycoconjugate to release saccharide from carrier; and (b) measuring DP of the released saccharide as described above. The invention provides a method for analysing a glycoconjugate composition, comprising the steps of: (a) separating unconjugated saccharide within the composition from conjugated saccharide; and (b) measuring DP of the unconjugated and/or conjugated saccharide as described above.

The invention also provides a method for releasing a vaccine for use by physicians, comprising the steps of: (a) manufacturing a vaccine comprising a conjugate of a capsular saccharide, wherein the saccharide comprises sialic acid monosaccharide subunits and non-sialic acid monosaccharide subunits; (b) analysing DP of saccharide in the vaccine as described above; and, if the results from step (b) indicate a DP acceptable for clinical use, (c) releasing the vaccine for use by physicians. Step (b) may be performed on a packaged vaccine or on a bulk vaccine prior to packaging.

Mixed Saccharides

The invention allows DP analysis in compositions that comprise meningococcal capsular saccharides that include sialic acid. The compositions may also comprise further capsular saccharides (e.g. a capsular saccharide from serogroup A of N. meningitidis, a capsular saccharide from H. influenzae b, etc.) provided that these saccharides do not contain sialic acids, which would interfere with the overall analysis. Where more than one saccharide in a composition includes sialic acid residues then the principles disclosed in reference 58 can be used to distinguish the different saccharides.

The capsular saccharide of serogroup A meningococcus is a homopolymer of ($\alpha$1→6)-linked N-acetyl-D-mannosamine-1-phosphate, with partial O-acetylation in the C3 and C4 positions. The acetyl groups can be replaced with blocking groups to prevent hydrolysis [10], and such modified saccharides are still serogroup A saccharides within the meaning of the present invention.

The Hib capsular saccharide is a polymer of ribose, ribitol, and phosphate. The saccharide is known as 'PRP' (poly-3-$\beta$-D-ribose-(1,1)-D-ribitol-5-phosphate).

Saccharide Components Other than Capsular Saccharides

It is preferred that compositions for analysis by the invention do not include sialic acid in free form (other than any background monosaccharides derived from capsular saccharide hydrolysis). If free sialic acid is present, however, then there are two general ways in which interference problems can be minimised or avoided. First, initial levels of free sialic acid can be measured and then subtracted from the levels measured in the depolymerised mixture. Second, free sialic acid can be removed from the composition prior to analysis e.g. by filtration or dialysis. Ultrafiltration membranes can be used to remove low molecular weight components.

Non-saccharide Components

As well as analysing saccharides in a composition, the process may include analysis of other components or properties e.g. osmolality, pH, degree of polymerisation for individual saccharides or conjugates, protein content (particularly for carrier proteins), aluminium content, detergent content, preservative content, etc.

The invention provides a method for preparing a vaccine composition, comprising a step of DP analysis of a saccharide according to the invention, and a step of pH measurement of the composition, optionally followed by a step of adjusting the pH of the composition to a desired value e.g. between 6 and 8, or about 7.

The invention also provides a method for preparing a vaccine composition, comprising the steps of: (a) providing DP-analysed capsular saccharide as described above; (b) conjugating the DP-analysed saccharide to one or more carrier proteins; (c) optionally, analysing the bulk vaccine for pH and/or other properties; and, if the results from step (c) indicate that the bulk vaccine is acceptable for clinical use, (d) preparing and packaging the vaccine for human use from the bulk. Step (c) may involve assessment of minimum saccharide concentration, assessment of unconjugated:conjugated saccharide ratio, etc. Step (d) may involve packaging into unit dose form or in multiple dose form e.g. into vials or into syringes. A typical human dose for injection has a volume of 0.5 ml.

The invention also provides a method for preparing a vaccine composition, comprising the steps of: (a) providing DP-analysed capsular saccharide from serogroup W135 and/or Y, as described above; (b) conjugating the DP-analysed saccharide to one or more carrier proteins, to give conjugated saccharide; and (c) mixing the conjugated saccharide with one or more further antigens e.g. with a capsular saccharide antigen from serogroup C of *N. meningitidis*.
    a capsular saccharide antigen from serogroup A of *N. meningitidis*.
    a protein antigen from serogroup B of *N. meningitidis*.
    preparations of *N. meningitidis* serogroup B microvesicles [59], 'native OMVs' [60], blebs or outer membrane vesicles [e.g. refs. 61 to 66 etc.].
    a saccharide antigen from *Haemophilus influenzae* type b.
    an antigen from *Streptococcus pneumoniae*, such as polyvalent conjugated saccharide antigens [e.g. refs. 67 to 69].
    an antigen from hepatitis A virus, such as inactivated virus [e.g. 70, 71].
    an antigen from hepatitis B virus, such as the surface and/or core antigens [e.g. 71, 72].
    an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 73 & 74]. Cellular pertussis antigens may be used.
    a diphtheria antigen, such as a diphtheria toxoid [e.g. chapter 3 of ref. 75] e.g. the $CRM_{197}$ mutant [e.g. 76].
    a tetanus antigen, such as a tetanus toxoid [e.g. chapter 4 of ref. 75].
    polio antigen(s) [e.g. 77, 78], such as IPV.

Such antigens may be adsorbed to an aluminium salt adjuvant (e.g. a hydroxide or a phosphate). Any further saccharide antigens are preferably included as conjugates.

Batch-to-Batch Consistency

For human vaccine manufacture, conjugated saccharides should be subjected to quality control before conjugation (e.g. the saccharide and the carrier protein), after conjugation, after formulation and after mixing. Prior art methods for DP measurement do not relate to the saccharides from serogroups W135 and Y. With the invention, however, DP measurement for these two serogroups is now possible, and can be combined with methods for DP measurement of serogroups A and C [5]. Moreover, the processes of the invention are reliable and consistent, and thus allow valid comparisons of different batches of mixed A/C/W135/Y conjugates, where this was not possible with prior art methods. Different batches of mixed conjugate vaccines can thus be prepared, assayed, and consistent batches can be selected for release and use, whereas aberrant batches can be rejected.

The invention provides two batches of a vaccine, wherein: (a) both of the batches of vaccine comprise: (i) a conjugate of a capsular saccharide from serogroup A of *Neisseria meningitidis*; (ii) a conjugate of a capsular saccharide from serogroup C of *Neisseria meningitidis*; (iii) a conjugate of a capsular saccharide from serogroup W135 of *Neisseria meningitidis*; (iv) a conjugate of a capsular saccharide from serogroup Y of *Neisseria meningitidis*; (b) the DP of the serogroup A saccharide in the first batch is $A_1$ and the DP of the serogroup A saccharide in the second batch is $A_2$; (c) the DP of the serogroup C saccharide in the first batch is $C_1$ and the DP of the serogroup C saccharide in the second batch is $C_2$; (d) the DP of the serogroup W135 saccharide in the first batch is $W_1$ and the DP of the serogroup W135 saccharide in the second batch is $W_2$; (e) the DP of the serogroup Y saccharide in the first batch is $Y_1$ and the DP of the serogroup Y saccharide in the second batch is $Y_2$; (f) the ratios $A_1/A_2$, $C_1/C_2$, $W_1/W_2$ and $Y_1/Y_2$ are each between 0.90 and 1.10, and preferably are each between 0.95 and 1.05.

The ratios specified in (f) may be based on a single sample from each batch being compared, but will typically be based on average values (e.g. means) from multiple samples of each batch. Thus the two batches may be subjected to multiple sampling, and each sample may be subjected to multiple measurements of $A_1$, $A_2$, $C_1$, $C_2$, $W_1$, $W_2$, $Y_1$ and $Y_2$, with averages then being calculated for each batch, and with the averages being used to calculate the necessary ratios.

Each batch (or lot) of vaccine will have been prepared separately. For example, two different batches can be made by separate mixings of the same bulk single conjugates, or by mixing bulk single conjugates that were separately prepared. Different samples of the same bulk mixture are not different batches, as these samples are not subject to the batch-to-batch variations that result from differences that arise when preparing mixtures of different conjugates.

In addition to characteristics (a) to (f) as specified above, the two batches may additionally be characterised by: (g) the concentration of unconjugated serogroup A saccharide in the first batch is $A_3$; (h) the concentration of unconjugated serogroup A saccharide in the second batch is $A_4$; (i) the concentration of unconjugated serogroup C saccharide in the first batch is $C_3$; (j) the concentration of unconjugated serogroup C saccharide in the second batch is $C_4$; (k) the concentration of unconjugated serogroup W135 saccharide in the first batch is $W_3$; if applicable, (l) the concentration of unconjugated serogroup W135 saccharide in the second batch is $W_4$; (m) the concentration of unconjugated serogroup Y saccharide in the first batch is $Y_3$; (n) the concentration of unconjugated serogroup Y saccharide in the second batch is $Y_4$; (o) the ratios $A_3/A_4$, $C_3/C_4$, $W_3/W_4$ and $Y_3/Y_4$ are each between 0.90 and 1.10, and preferably are each between 0.95 and 1.05.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

It will be appreciated that sugar rings can exist in open and closed form and that, whilst closed forms are shown in structural formulae herein, open forms are also encompassed by the invention.

BRIEF DESCRIPTION OF DRAWINGS

FIG. 21 is a further gradient elution profile of MenW135 oligosaccharide. FIG. 21A shows a standard sample, and FIG. 21B shows the MenW135 material.

MODES FOR CARRYING OUT THE INVENTION

Preparation of Standard Oligosaccharide Solutions

Figure 1:
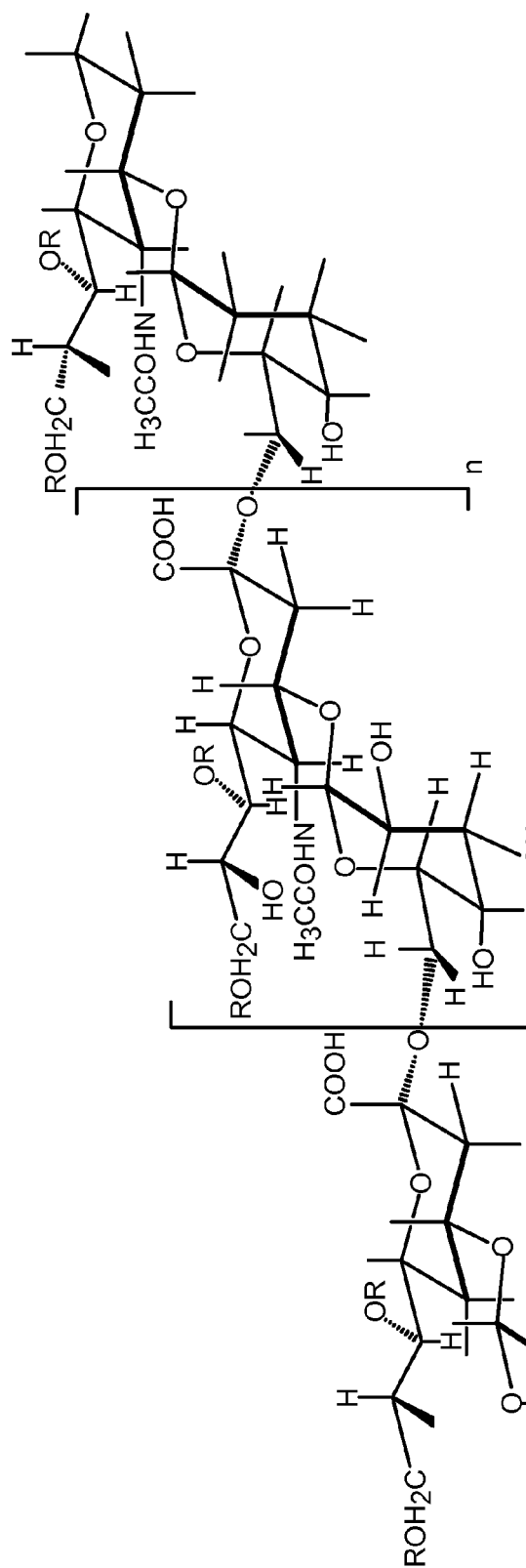
FIGS. 1 and 2 show structural formulae for the capsular saccharides of meningococcal serogroups W135 (1), and Y (2).
Figure 2:
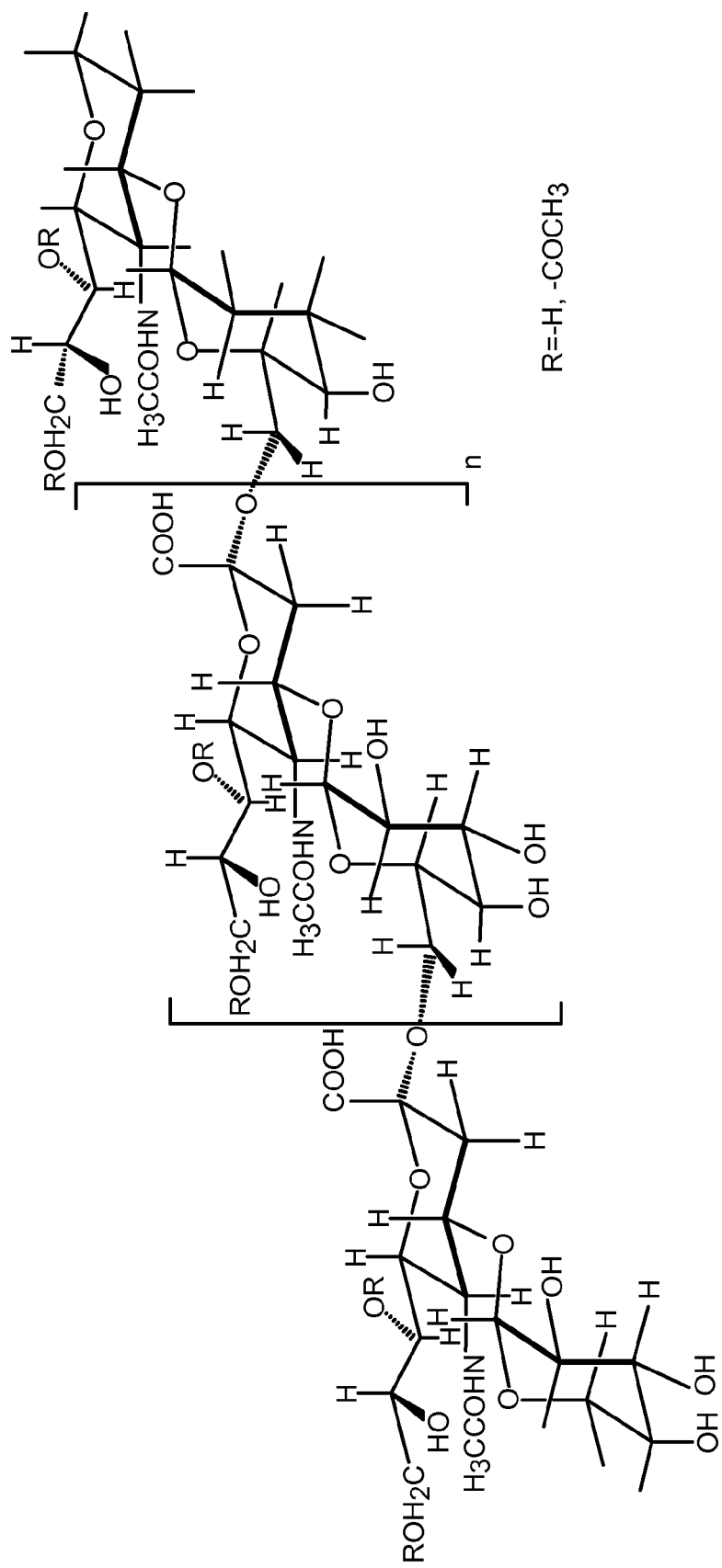
Figure 3:
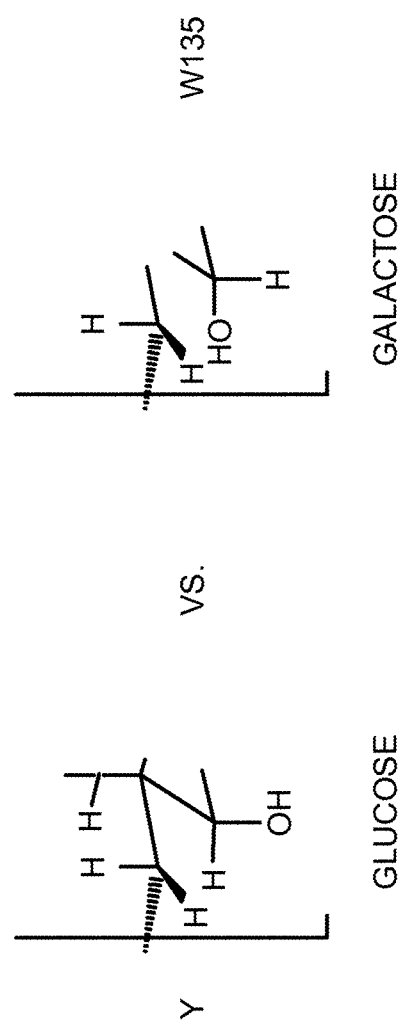
FIG. 3 shows the difference between serogroups W135 and Y.

Purified serogroup W135 and Y capsular polysaccharide (CPS) were prepared using the methods described in reference 79. They was supplied as a 10 mg/ml solution in 0.01 M acetic acid. To hydrolyse the CPS, they were heated to 70-80° C. for a prolonged period. During the hydrolysis, samples were obtained from the solutions for analysis, and were cooled and neutralized after being extracted. Fragments resulting from this hydrolysis have terminal sialic acid residues, rather than terminal glucose or galactose residues. Oligosaccharides were then purified by ion exchange chromatography on a Q-Sepharose column, which separates on the basis of size and charge. For initial normalisation, sialic acid content was measured by a modified Svennerholm method [80], whereby the absorbance was read at 564 nm. Specific fractions were isolated and analysed by NMR, by electrospray mass spectrometry and by HPAEC.

HPAEC analysis of the oligosaccharides used either a CarpoPac PA100 or an IonPac AS11 column (both 4×250 mm) on a Dionex DX-500 chromatography system fitted with a GP40 pump, ED40 detector and AS3500 auto sampler. Separations were performed at room temperature using a flow rate of 1.0 ml/min.

The PA100 column used the following eluents: A) sodium acetate 500 mM+sodium hydroxide 100 mM and B) sodium hydroxide 100 mM. An initial isocratic elution with 10% A (15 min) was followed by a linear gradient elution from 10% to 100% A over 50 min. The AS11 column used the following eluents: A) sodium hydroxide 100 mM and B) water, with a linear gradient elution from 5% to 100% A over 50 min.

Eluates were monitored using a pulsed electrochemical detector (ED40) in the pulsed amperometric mode with a gold working electrode and an Ag/AgCl reference electrode. A triple-potential waveform was applied using the following settings: E1=0.05 V, t1=400 ms; E2=0.75 V, t2=200 ms; E3=0.15 V, t3-400 ms. Integration occurs from 200 ms to 400 ms during E1 application. The resulting chromatographic data were integrated and processed using Peak Net data reduction software (Dionex).

The CarboPac PA100 HPAEC gave a profile of MenW135 and MenY oligosaccharides. Calibration of the spectra was performed by comparing purified and pool oligosaccharide chromatograms, with parallel characterisation of purified oligosaccharides by ESI-MS to allow correlation between the peak number in the chromatogram and the DP of the eluting oligosaccharides.

ESI mass spectrometry was performed on a Micromass ZQ-4000 mass analyser equipped with an electrospray ionization source. The instrument was calibrated using a sodium iodide (2 g/l) and caesium iodide (50 mg/l) diluted with isopropyl alcohol/water 50/50 (v/v). The capillary voltage was 3 kV, the cone voltage was 60 V. Samples were dissolved in 50% (v/v) aqueous acetonitrile+0.1% formic acid and injected with flow rate of 10 μl/min. The spectra were recorded in positive ion mode with scanning range from 200 to 2000 m/z.

Figure 4:
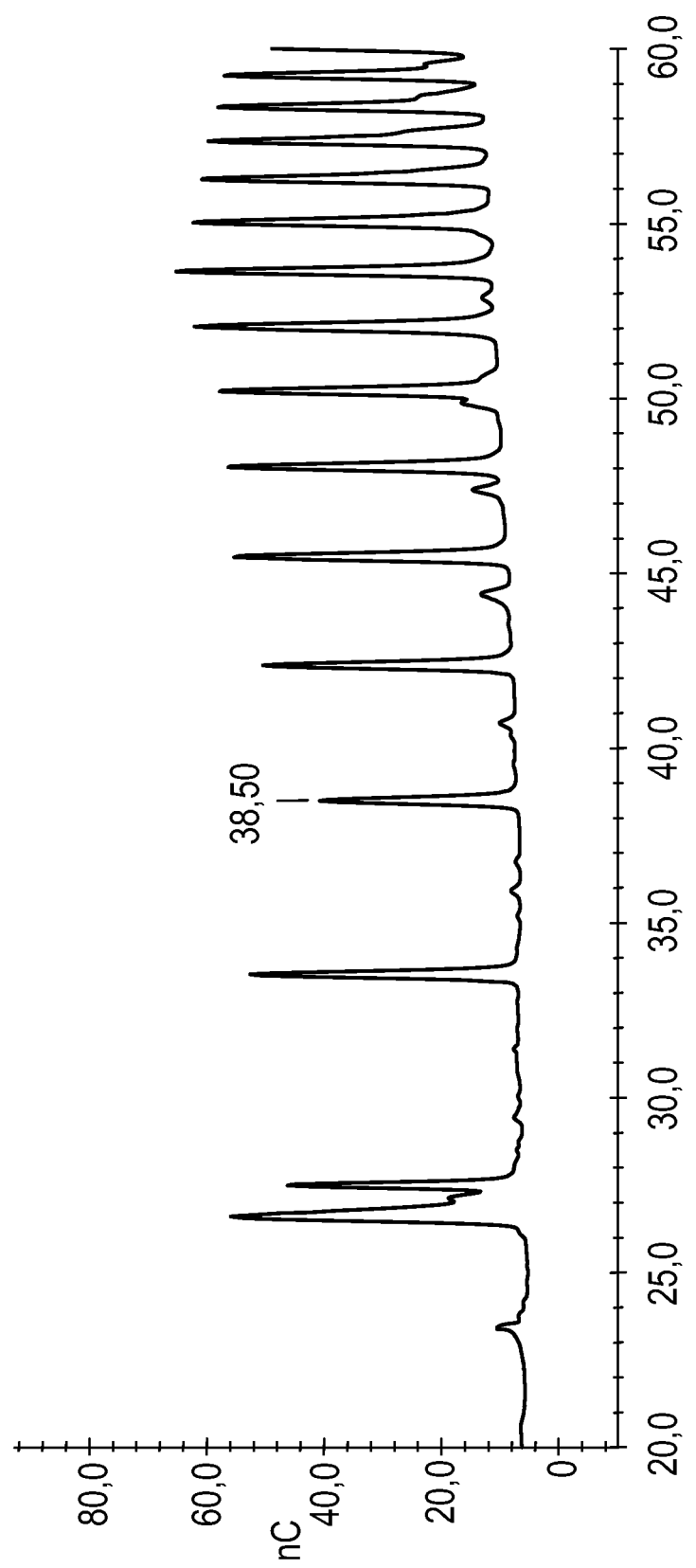
FIGS. 4 and 5 show chromatograms of MenY saccharides before (4) and after (5) size separation.
Figure 5:
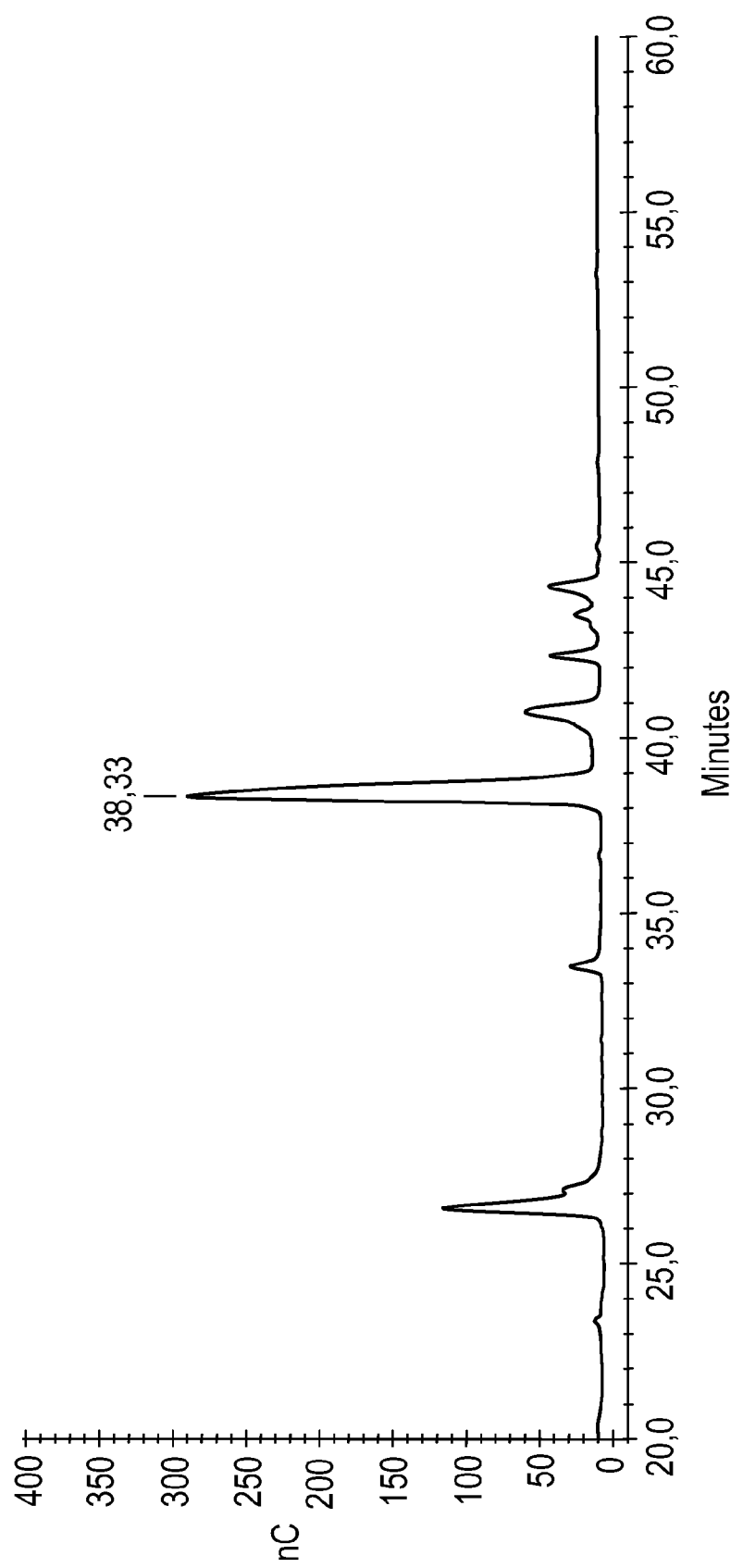

FIGS. 4 and 5 show HPAEC chromatograms (PA100 column) for the MenY oligosaccharide mixture before (FIG. 4) and after (FIG. 5) Q-Sepharose separation. ESI analysis of the peak at ~38 minutes confirmed that it is a MenY oligosaccharide with a DP of 4 (FIG. 7). Similar experiments were performed for MenW135, with FIG. 6 showing an ESI spectrum of a DP3 oligosaccharide.

In the ESI analysis, a single molecular species can show multiple molecular ions in the spectrum, corresponding to the parent molecule with varying numbers of O-acetyl substitution and sodium ions adduct. Sodium adduct ions can arise from the presence of some amounts of sodium during sample analysis and are commonly observed in the mass spectra of oligosaccharides. Furthermore the parent molecule can assume different number of positive charges, and so an oligosaccharide molecule can produce many different positive ions, depending on O-acetyl substitution, sodium adducts and number of positive charge. There are thus large numbers of positive ions in FIGS. 6 and 7.

Figure 6:
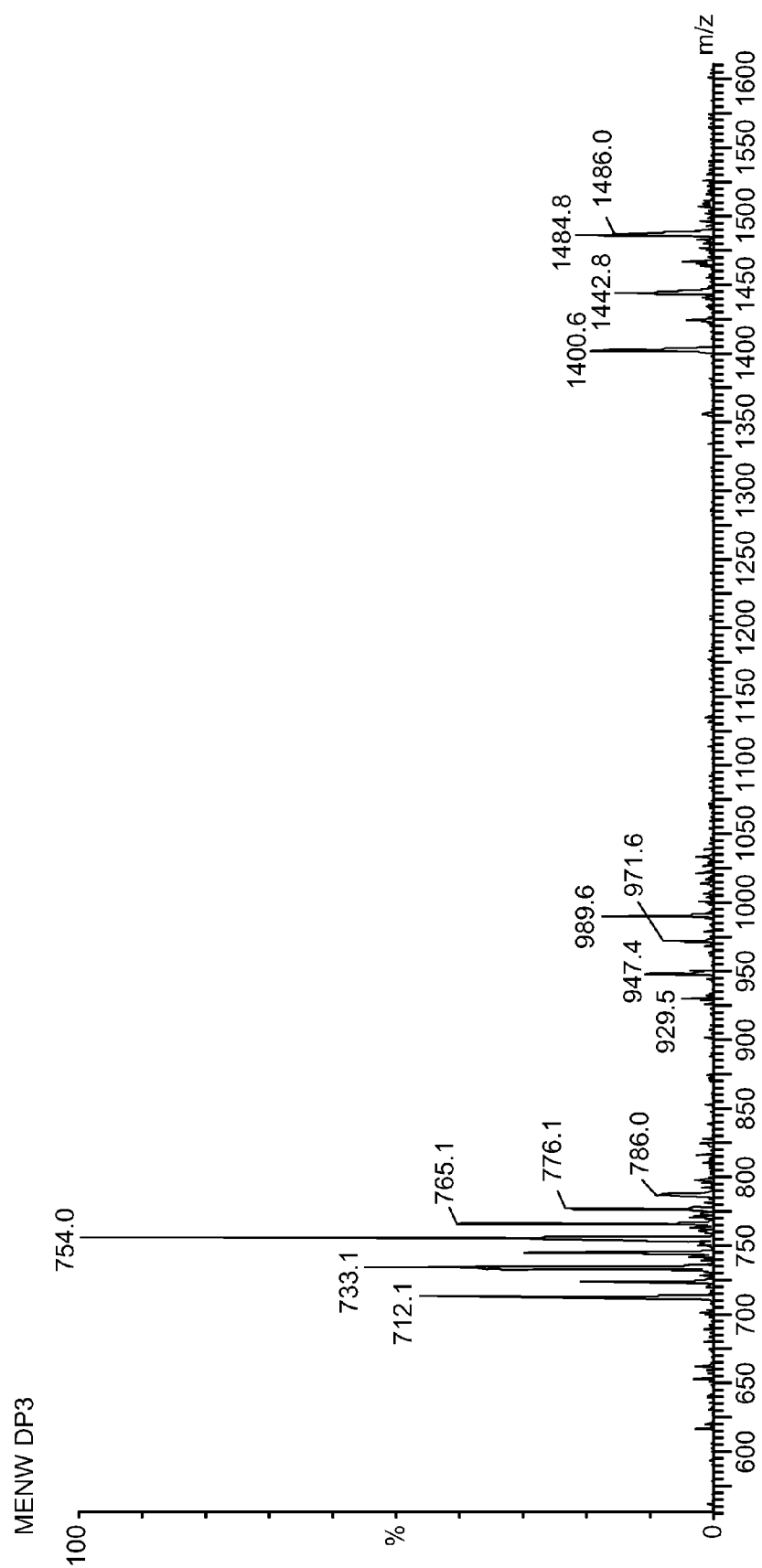
FIGS. 6 and 7 show ESI spectra for MenW135 (6) and MenY (7) saccharides.
Figure 7:
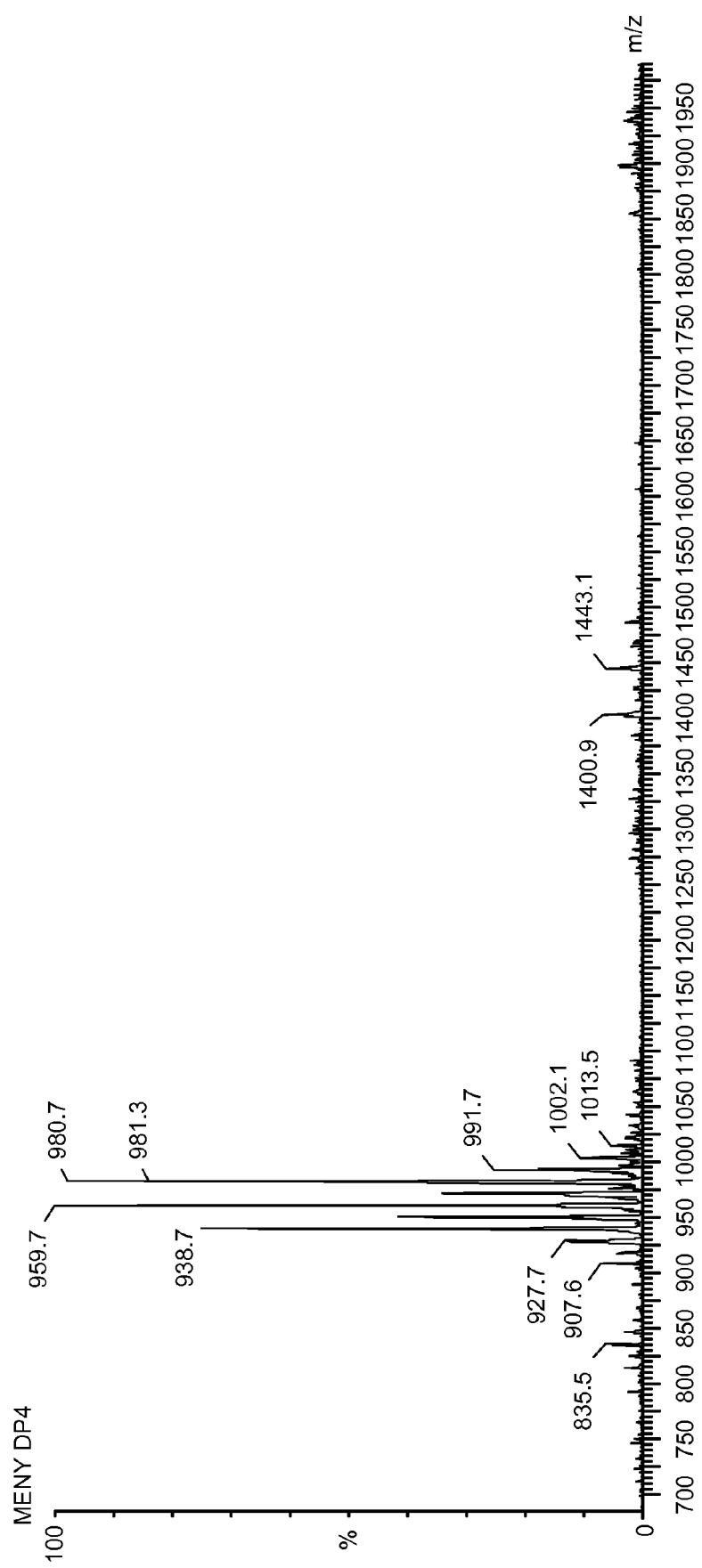

In FIG. 6, the peaks between 700-800 and 1400-1526 m/z correspond to double and single-charged ions respectively, resulting from the addition of sodium cations and O-Acetyl groups. They were assigned to the following monoisotopic masses, which correspond to those of a trimer oligosaccharide (MenW135 DP3):

| Observed ions | Expected ions[a] | O-acetyl[b] | Na[c] | charge |
|---|---|---|---|---|
| 1400.6 | 1401.4 | 0 | 1 | 1 |
| 1442.8 | 1443.4 | 1 | 1 | 1 |
| 1484.8 | 1485.4 | 2 | 1 | 1 |
| 1526.5 | 1527.4 | 3 | 1 | 1 |
| 712.0 | 712.7 | 0 | 2 | 2 |
| 723.0 |  | 1 |  | 2 |
| 733.1 | 733.7 | 1 | 2 | 2 |
| 744.2 |  | 2 |  |  |
| 754.0 | 754.7 | 2 | 2 | 2 |
| 765.1 |  | 3 |  | 2 |
| 775.6 | 775.7 | 3 | 2 | 2 |

[a]theoretical ions calculated from monoisotopic masses by MW calculator (MassLynx software)
[b]number of O-acetyl substituents
[c]number of sodium as counter ions In FIG. 7, the peaks between 900-1100 and 1800-2000 m/z correspond to double and single-charged ions respectively, resulting from the addition of sodium cations and O-Acetyl groups. They were assigned to the following monoisotopic masses showed in Tab. 2, which corresponds to those of a tetramer oligosaccharide (MenY DP4):

| Observed ions | Expected ions | O-acetyl | Na | charge |
|---|---|---|---|---|
| 1896.0 | 1896.6 | 1 | 1 | 1 |
|  | 916.8 | 0 | 0 | 2 |
| 927.7 | 927.8 | 0 | 1 | 2 |
| 938.7 | 937.8 | 1 | 0 | 2 |
| 949.6 | 949.3 | 1 | 1 | 2 |
| 959.7 | 958.8 | 2 | 0 | 2 |

-continued

| Observed ions | Expected ions | O-acetyl | Na | charge |
|---|---|---|---|---|
| 971.4 | 970.3 | 2 | 1 | 2 |
| 980.8 | 979.8 | 3 | 0 | 2 |
| 991.7 | 991.3 | 3 | 1 | 2 |
| 1003.3 | 1002.8 | 3 | 2 | 2 |

NMR samples were prepared by dissolving lyophilised oligosaccharides in 750 μL 99.9% $D_2O$ (Aldrich™) to give 10-15 mM concentrated solutions. 5 mm Wilmad™ NMR tubes were used for every experiment. NMR spectra were recorded at 298 K on a Bruker™ NMR Spectrometer Avance DRX 600 MHz, equipped with a 5 mm TBI triple resonance heteronuclear probe and a BGU unit. Bruker XWINNMR 3.0 software was used for data acquisition and processing. $^1H$ standard spectral acquisition conditions were to collect 32 k data points over a spectral window of 6000 Hz with 4 scans and 10 sec of relaxation delay. $^1H$ NMR spectra were Fourier-transformed after applying a 0.1 Hz line broadening function and referenced relative to mono-deuterated water at 4.79 ppm. $^{13}C$ and 2D NMR experiments (double-quantum filtered COSY and HSQC) were carried out to assign the $^1H$ spectra of oligosaccharides.

Figure 8A:
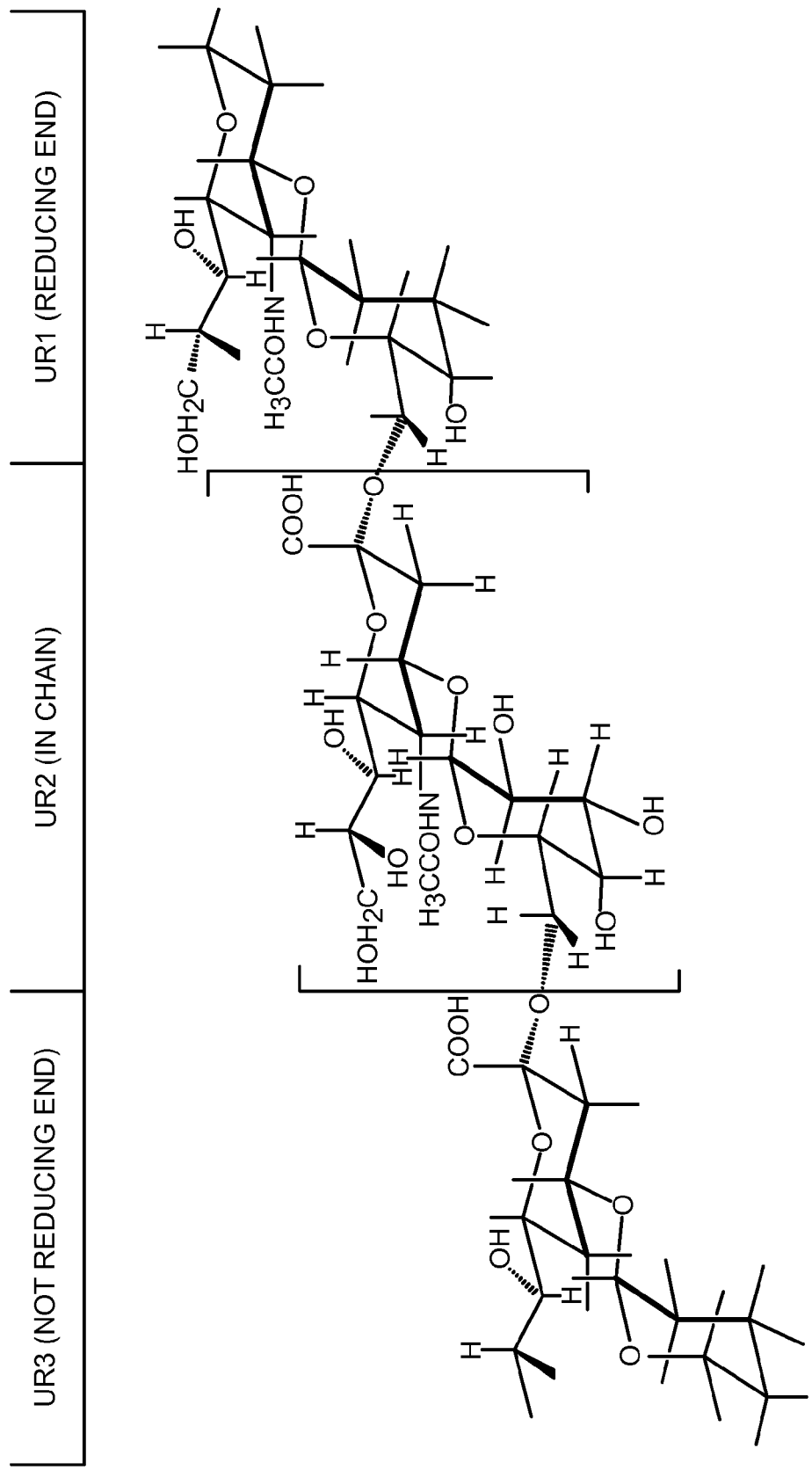
FIG. 8 shows the structure of the MenW135 DP3 saccharide above its $^1$H NMR spectrum.
Figure 9A:
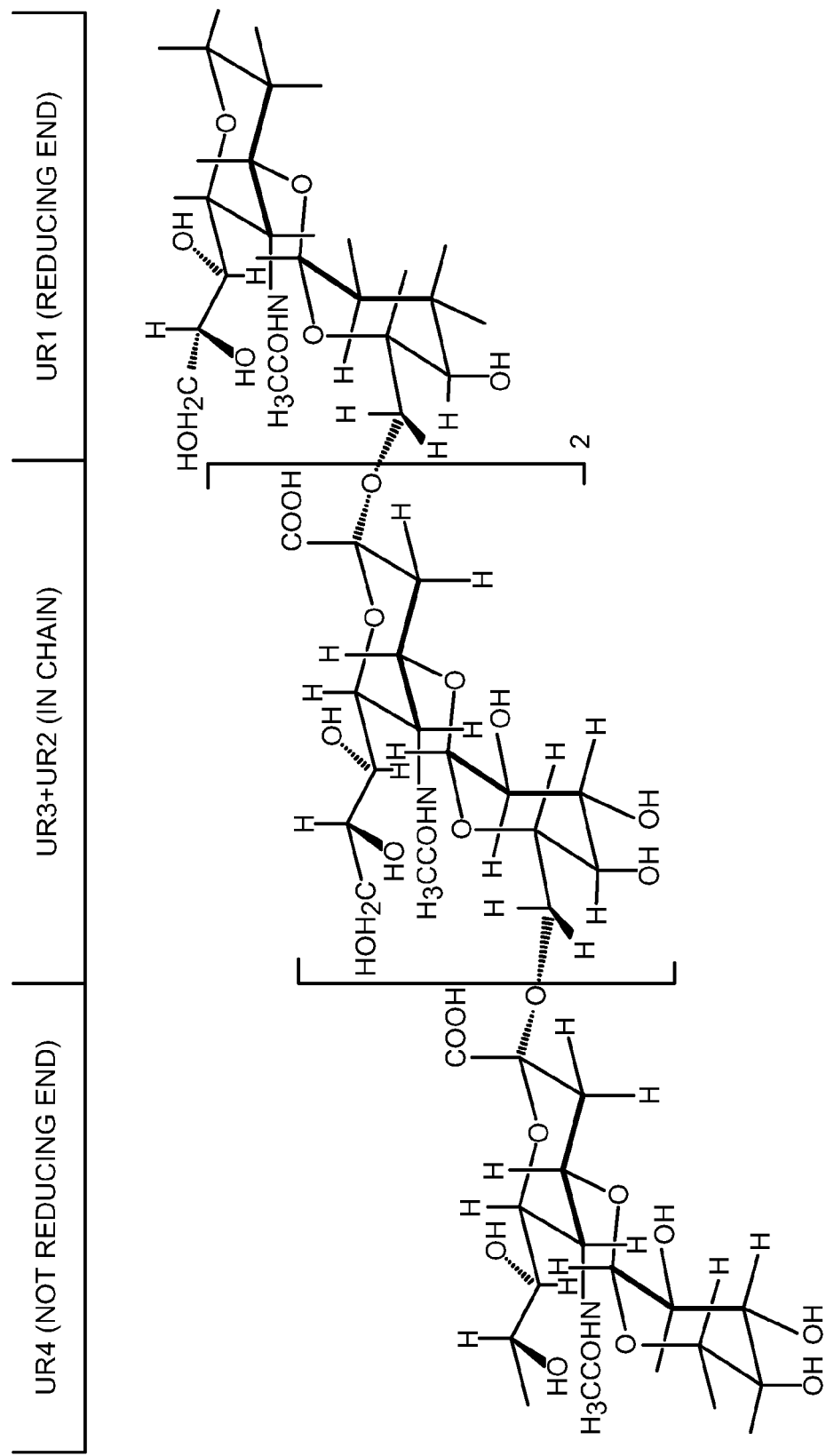
FIG. 9 shows the same for MenY DP4 saccharide.
Figure 9B:
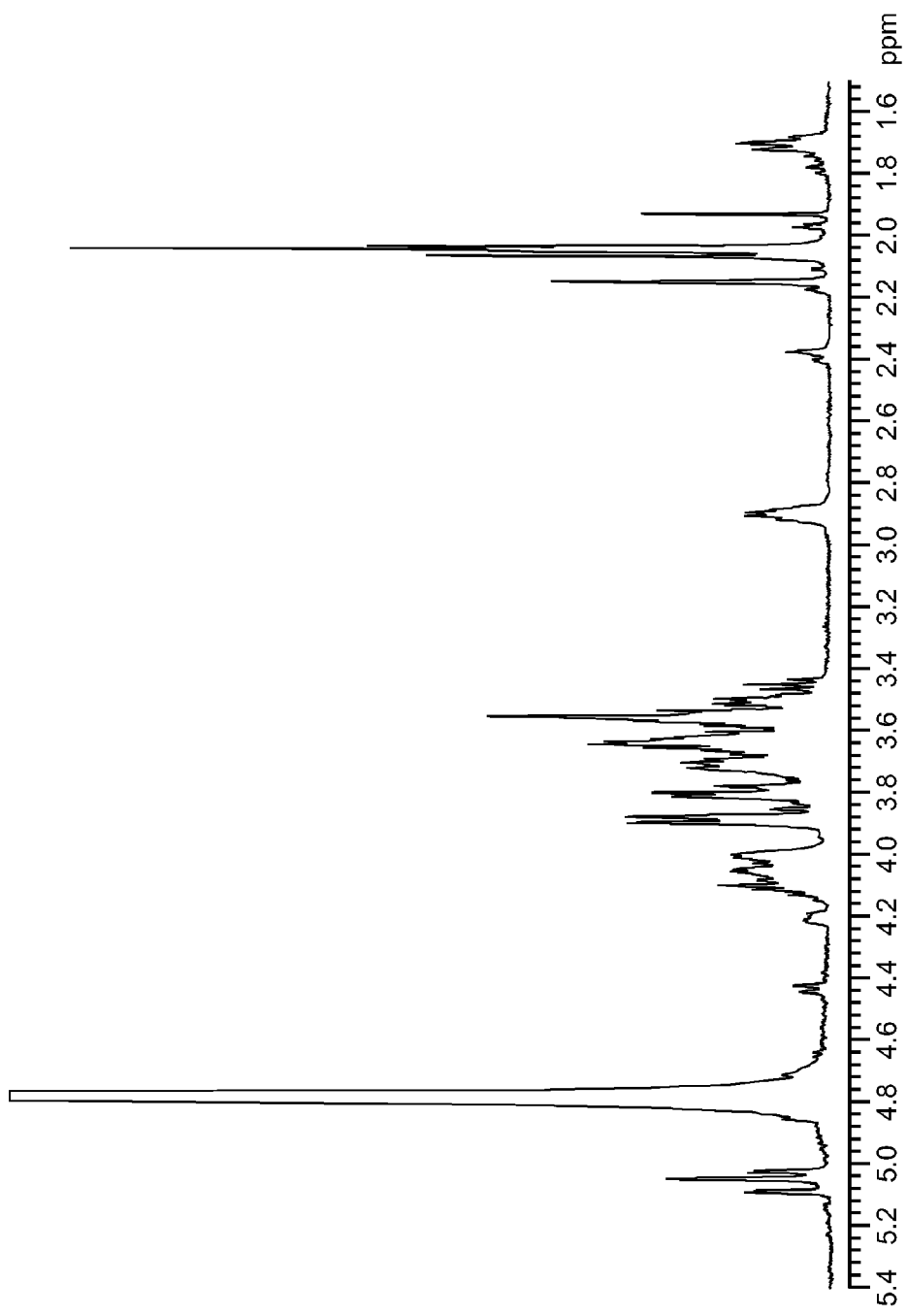

Proton NMR spectra of the meningococcal W135 and Y oligosaccharides were assigned by comparison with published data [81] and by two-dimensional proton-proton COSY and proton-carbon HSQC correlation spectra. In addition to proton chemical shifts, the homonuclear and heteronuclear coupling constants offered a wealth of structural information. The high-resolution NMR spectra of W135 (FIG. 8) and MenY (FIG. 9) oligosaccharides show relatively sharp signals which allow a particularly defined peak assignment of anomeric proton of Gal/Glc moieties and the H3 eq/axNeuNAc of NeuNAc moieties. These peaks are situated in spectral regions where there is no superposition with other signals that can complicate linear resolution. By expanding the spectrum, proton chemical shifts of signals could be determined:

| W135 | ppm | Y | ppm |
|---|---|---|---|
| $H_1^{Gal}{}_{UR1}$ | 5.112 | $H_1^{Glc}{}_{UR1}$ | 5.090 |
| $H_1^{Gal}{}_{UR2}$ | 5.095 | $H_1^{Glc}{}_{UR2}$ | 5.049 |
| $H_1^{Gal}{}_{UR3}$ | 5.087 | $H_1^{Glc}{}_{UR3}$ | 5.049 |
| $H_{3eq}^{NeuNAc}{}_{UR3}$ | 2.963 | $H_1^{Glc}{}_{UR4}$ | 5.025 |
| $H_{3eq}^{NeuNAc}{}_{UR2}$ | 2.905 | $H_{3eq}^{NeuNAc}{}_{UR4}$ | 2.918 |
| $H_{3eq}^{NeuNAc}{}_{UR1}$ | 2.434 | $H_{3eq}^{NeuNAc}{}_{UR3}$ | 2.907 |
| $H_{3ax}^{NeuNAc}{}_{UR1}$ | 1.762 | $H_{3eq}^{NeuNAc}{}_{UR2}$ | 2.897 |
| $H_{3ax}^{NeuNAc}{}_{UR2}$ | 1.707 | $H_{3eq}^{NeuNAc}{}_{UR1}$ | 2.400 |
| $H_{3ax}^{NeuNAc}{}_{UR3}$ | 1.687 | $H_{3ax}^{NeuNAc}{}_{UR1}$ | 1.782 |
| | | $H_{3ax}^{NeuNAc}{}_{UR2}$ | 1.726 |
| | | $H_{3ax}^{NeuNAc}{}_{UR3}$ | 1.705 |
| | | $H_{3ax}^{NeuNAc}{}_{UR4}$ | 1.705 |

The $^1H$ NMR spectra confirmed the molecular structure, identity and integrity of saccharide chains, and show the DP values of the samples: $DP_{MenW135} = 3$; $DP_{MenY} = 4$.

Thus the Q-Sepharose column was able to resolve oligosaccharides by DP, and the ESI and NMR analyses confirm that the oligosaccharide standards are: MenW135 DP3; and MenY DP4. These standards were analysed by the processes of the invention.

Chromatographic analysis of DP

Oligosaccharide samples were adjusted to contain 0.5 mg/ml sialic acid in 100 μl. These samples were treated with 100 μl $NaBH_4$ solution 40 mM in NaOH 10 mM. Samples were heated at 37° C. for 2 hours in a closed screw-cap test tube. To stop the reaction samples were then treated with 10 μl ammonium acetate 5M pH 6.0 and maintained at room temperature for 30 minutes. 200 μl methanol was added and samples were then dried on a Speed Vac concentrator fitted with a refrigerated condensation trap (Savant SC110) under vacuum for 1 hour.

Samples were reconstituted with 100 μl Milli-Q water and 100 μl TFA 4M (final concentration: 2M) and heated at 100° C. for 90 minutes. Hydrolysates were then dried on a Speed vac concentrator fitted with two refrigerated condensation trap (Savant SC 110).

For HPAEC-PAD analysis, samples were dissolved in 1.0 ml Milli-Q degassed water and then filtered (0.22 μm). Analysis of the hydrolysed products was performed on the same Dionex system, but using a Carbopac PA1 column (4×250 mm) with a Borate Trap guard column. This column and guard are better suited to monosaccharide analysis that the PA100 and AS11 columns. Isocratic elution with sodium acetate 50 mM+sodium hydroxide 20 mM was used in some experiments, and other experiments used gradient elution was used with the following eluents: A) sodium acetate 100 mM+sodium hydroxide 20 mM and B) sodium hydroxide 20 mM and with a gradient from 10% to 70% of A (curve 7). Eluates were analysed as described above.

This apparatus can distinguish sialic acid from sialitol, and can give quantitative results for each. The ratio of total (i.e. reduced and non-reduced) sialic acid to reduced sialic acid was used to calculate the DP of the starting oligosaccharides.

Figure 10:
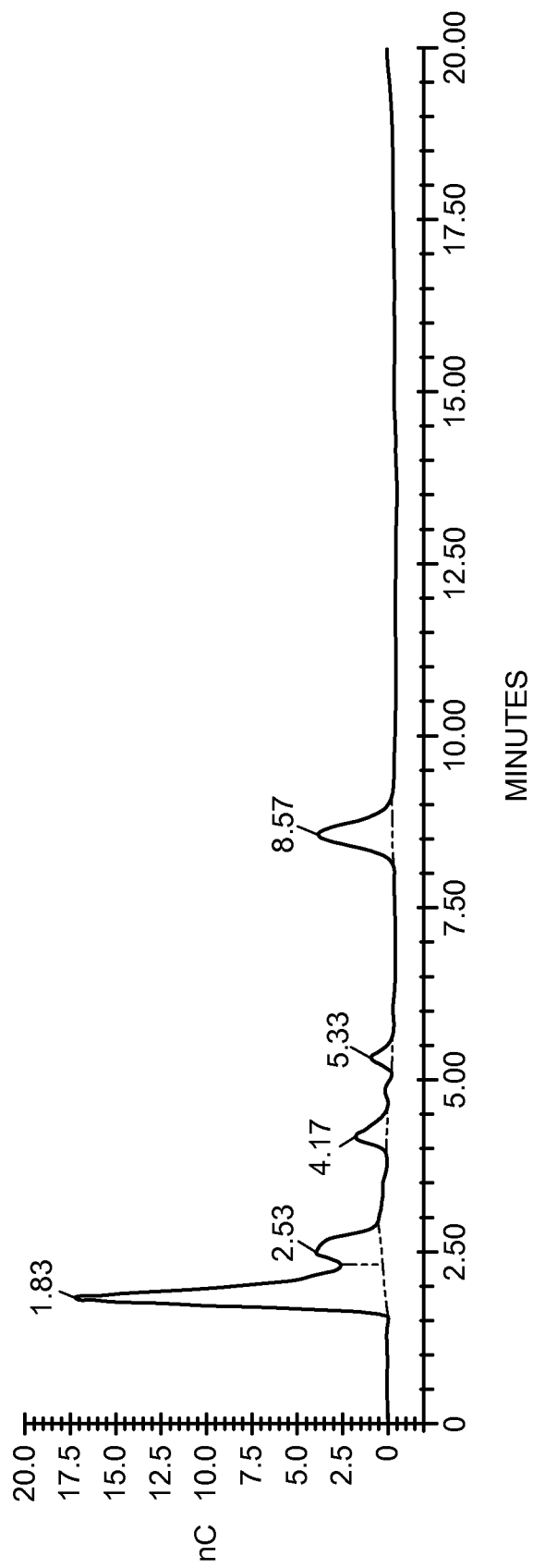
FIGS. 10 to 12 show isocratic elution profiles of sialic acid standard solutions.

For initial testing, a standard solution of pure sialic acid (Sigma, Steinheim, Germany) was prepared at 2.0 μg/ml and subjected to $NaBH_4$ reduction as described above. Samples were analysed at various time points by HPAEC with isocratic elution. Treatment with 0.04M $NaBH_4$ for 2 hours at 37° C. was found to give complete reduction of sialic acid in the standard. FIG. 10 shows a time zero sample, and FIG. 11 shows the 2 hour sample, with retention time decreasing from 8.5 to 4.7-5.0.

Figure 11:
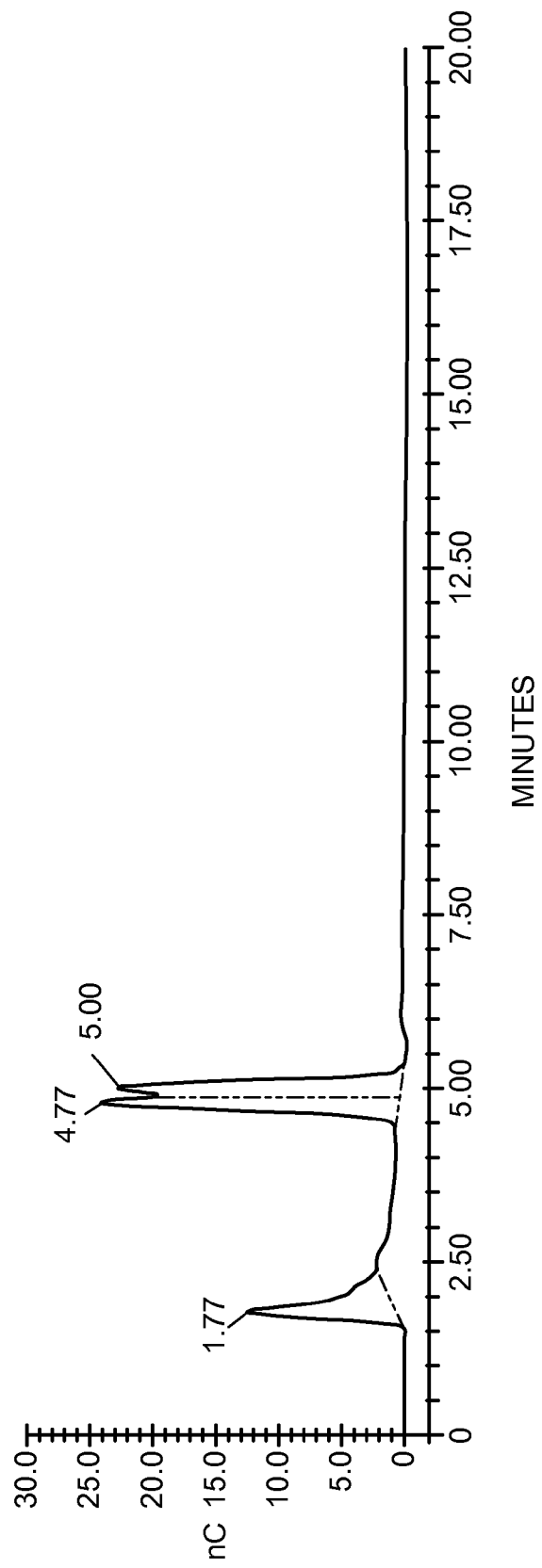
Figure 12:
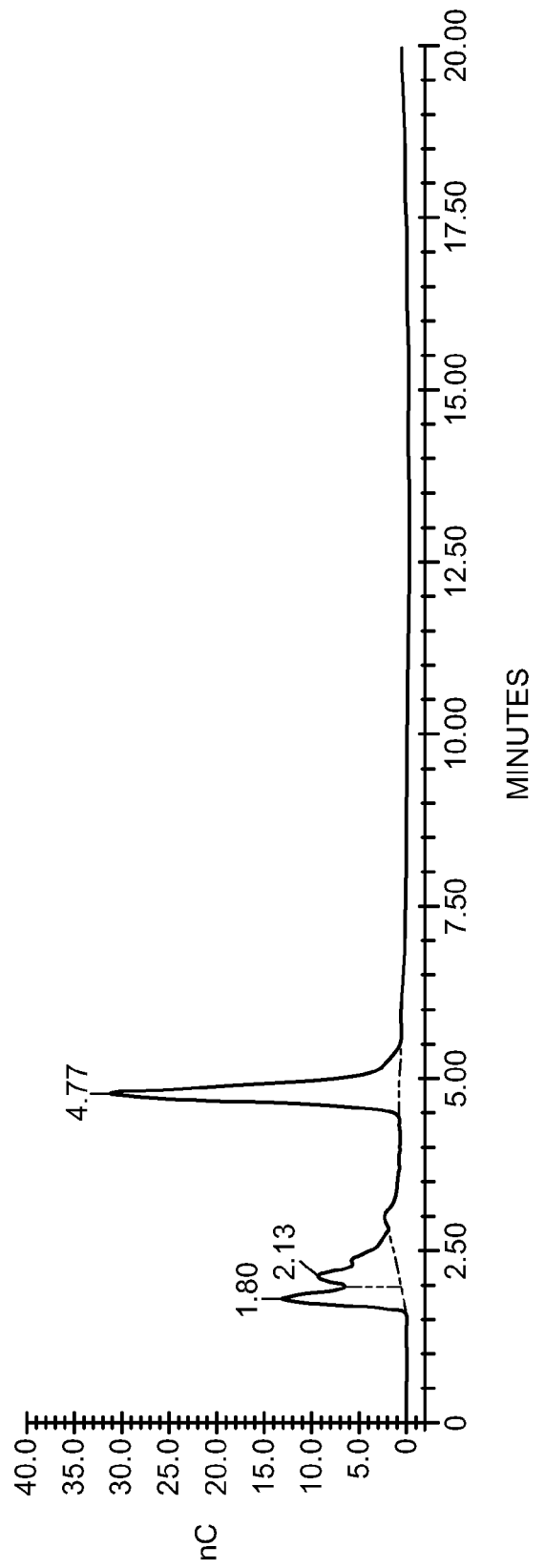

The double peak in FIG. 11 is due to unresolved diastereoisomers of sialitol [14]. Treatment of the sialic acid standard with 2M TFA for 90 minutes at 100° C. was able to remove the double peak (FIG. 12), thus giving a single peak for sialitol quantification. TFA hydrolysis is known to be suitable for saccharide cleavage, in terms of both efficiency and ease of removal [82-84], and has been used for analysis of several saccharide vaccines [82]. Thus the use of TFA for acid hydrolysis of saccharides has a triple purpose—efficient hydrolysis, efficient removal, and removal of peak splitting for sialitol.

Figure 20:
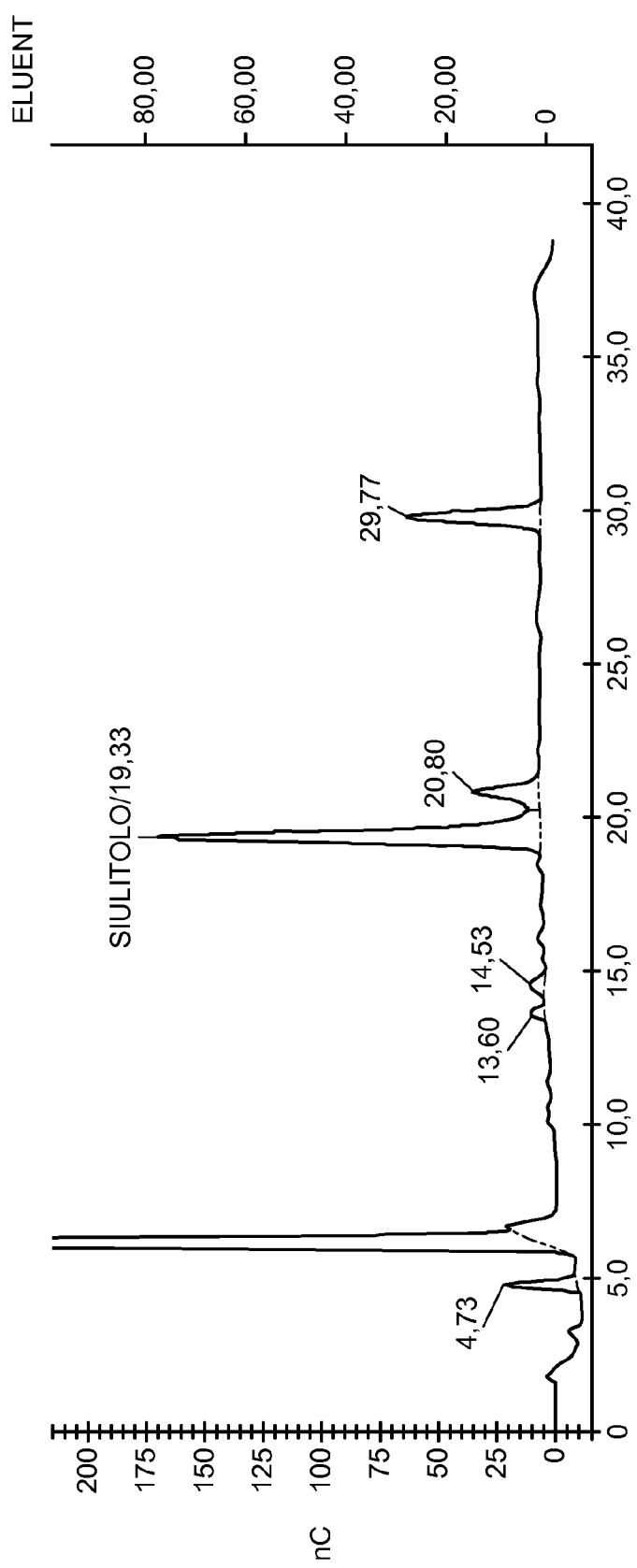
FIG. 20 is a gradient elution profile of MenW135 oligosaccharide. The left axis shows amperometric detection in nC; the right axis shows % eluent (100 mM Na-acetate+20 mM NaOH).

An oligosaccharide sample of MenY, with an expected DP ranging between 3 and 5, was treated as described, but isocratic conditions for chromatographic elution did not give good separation of the sialitol peak. An elution gradient was therefore used instead, which gave the chromatogram shown in FIG. 13. Sialitol and sialic acid had retention times of 19.3 and 29.8 minutes, respectively. A sample of MenW135 oligosaccharide with an expected DP ranging between 3 and 5 was analysed with the same method (FIG. 20). Sialitol is seen at 19.33 minutes and sialic acid is seen at 29.77.

Figure 13:
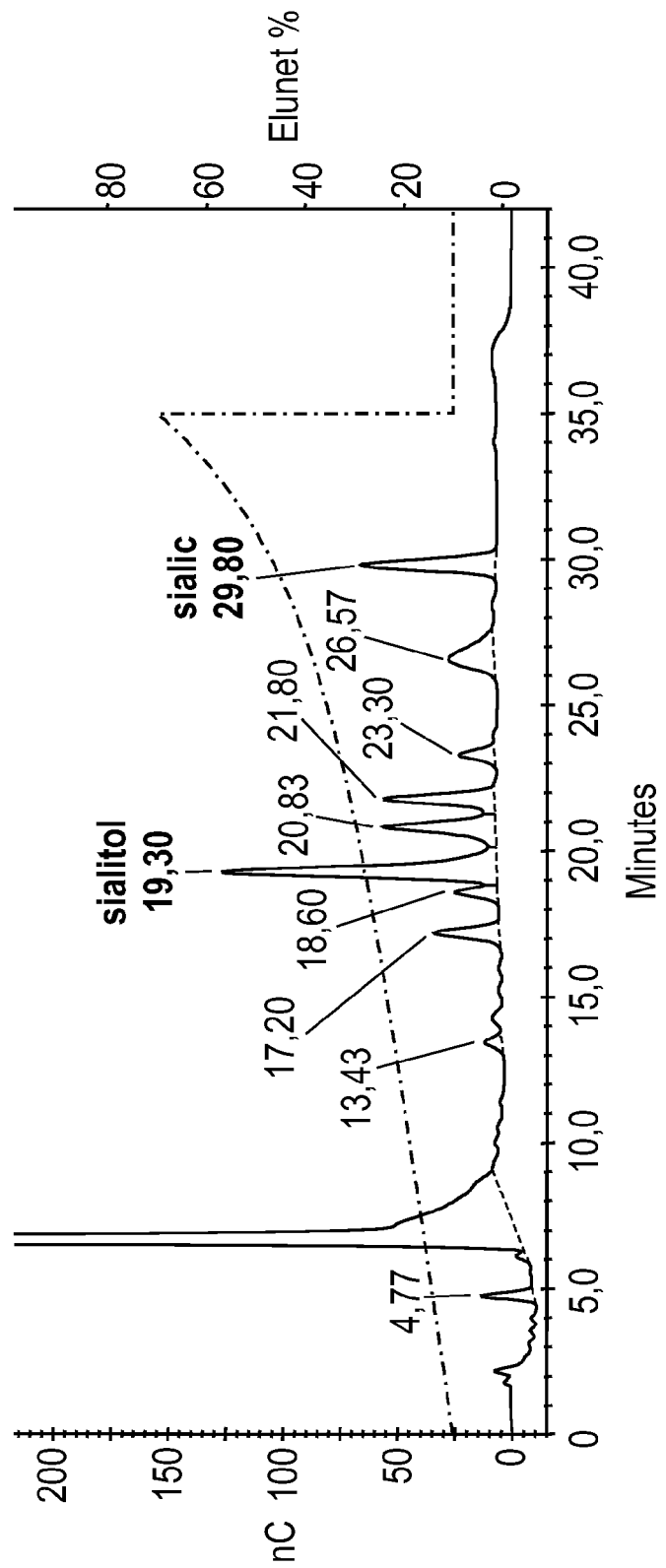
FIG. 13 shows a gradient elution profile of MenY oligosaccharide.
Figure 14:
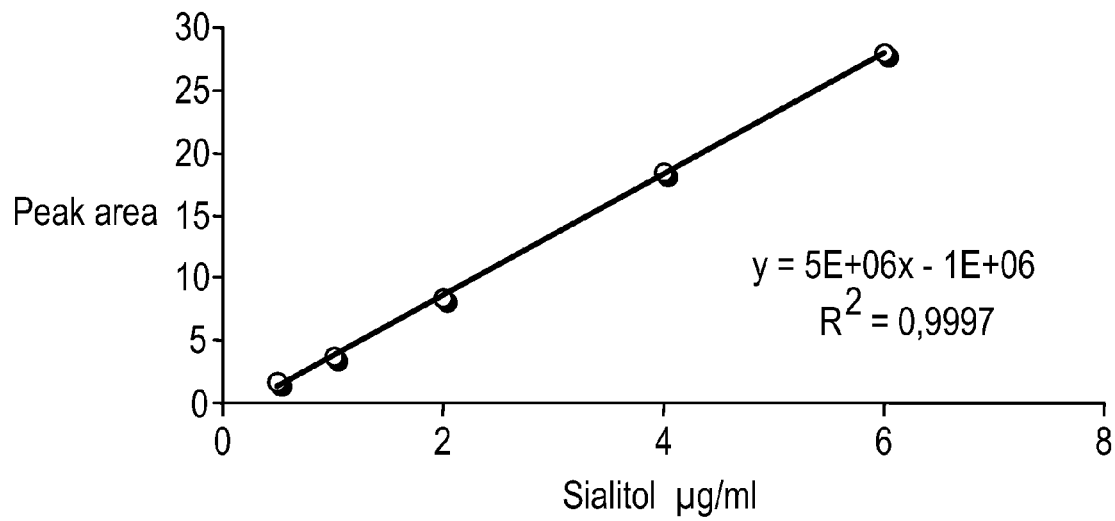
FIG. 14 shows a standard curve for sialitol.

To facilitate quantitative analysis of the FIG. 13 and FIG. 20 chromatograms, standard curves based on known sialic acid and sialitol concentrations were made. The standard curve used 0.5, 1.0, 2.0, 4.0 and 6.0 μg/ml sialic acid or sialitol. The linear response of the detector is shown in FIG. 14.

By comparison to these standard curves, amounts of sialitol and sialic acid could be quantified in the MenW135 and MenY samples. For example, the area under the 19.33 minutes peak in the MenW135 elution (FIG. 20) was calculated to be 44914068. By reference to the standard curve, the sialitol concentration was calculated to be 7.96 µg/ml. In a duplicate experiment a concentration of 8.05 µg/ml was seen. The two analyses give a mean value of 8.005 µg/ml. As the samples were diluted 10× prior to analysis then the original mean sialitol concentration was 80.05 µg/ml. Colorimetric detection of total sialic acid gave a concentration of 241.09 µg/ml. Taking account of the slight mass difference between sialic acid and sialitol, these concentrations were converted to molar concentrations (in fact, the mass difference is so slight that an excellent approximation is achieved without converting to moles) and the molar ratio was calculated as 3 (i.e. DP=3). Ratios calculated from results of two different duplicate analyses were as follows:

| Sample | Sialitol (µg/ml) | Sialic acid (µg/ml) | DP |
|---|---|---|---|
| Oligo-MenW | 80.5 | 241.09 | 3.0 |
| Oligo-MenW | 79.6 | 241.09 | 3.0 |
| Oligo-MenY | 62.7 | 303.64 | 4.8 |
| Oligo-MenY | 68.9 | 303.64 | 4.4 |

Repeatability of the sialitol measurement method was evaluated by analysing a single MenW135 sample for 4 replicates using three different pre-column borate traps. Results were as follows:

| Borate trap | Sialitol (µg/ml) | Sialic acid (µg/ml)* | DP | Average | Std Dev | CV % |
|---|---|---|---|---|---|---|
| 1 | 342.5 | 6484.2 | 18.9 | 18.7 | 0.2 | 0.9 |
|   | 345.7 | 6484.2 | 18.8 |   |   |   |
|   | 346.3 | 6484.2 | 18.7 |   |   |   |
|   | 350.2 | 6484.2 | 18.5 |   |   |   |
| 2 | 335.7 | 6484.2 | 19.3 | 19.2 | 0.1 | 0.5 |
|   | 339.5 | 6484.2 | 19.1 |   |   |   |
|   | 338.3 | 6484.2 | 19.2 |   |   |   |
|   | 336.0 | 6484.2 | 19.3 |   |   |   |
| 3 | 328.0 | 6484.2 | 19.8 | 19.7 | 0.4 | 1.9 |
|   | 335.5 | 6484.2 | 19.3 |   |   |   |
|   | 334.3 | 6484.2 | 19.4 |   |   |   |
|   | 321.8 | 6484.2 | 20.2 |   |   |   |

*Measured separately, duplicate analysis

The results thus show a good repeatability (CV %<2%).

A 10 mg/ml solution of full-length MenY or MenW135 CPS in 0.01 M acetic acid was heated to 70-80° C. During hydrolysis, samples were taken for average DP determination to track the progress of the reaction for up to 6 hours. Samples were rapidly frozen and maintained at −20° C. prior to duplicate analysis using an IonPac AS11 column. Results were as follows:

| | MenW135 | | | MenY | | |
|---|---|---|---|---|---|---|
| Time (hours) | Sialitol (µg/ml) | Sialic acid (µg/ml) | Average DP | Sialitol (µg/ml) | Sialic acid (µg/ml) | Average DP |
| 0.5 | 45.40 | 5338.4 | 117.6 | 61.56 | 5903.0 | 95.9 |
| 1.0 | 74.12 | 5351.5 | 72.2 | 94.84 | 5803.6 | 61.2 |
| 1.5 | 125.63 | 5519.9 | 43.9 | 125.87 | 5764.0 | 45.8 |
| 2.0 | 139.49 | 5620.2 | 40.3 | 170.92 | 5790.0 | 33.9 |
| 2.5 | 195.40 | 5611.8 | 28.7 | 218.13 | 5808.4 | 26.6 |
| 3.0 | 235.55 | 5555.7 | 23.6 | 237.17 | 6294.1 | 26.5 |
| 3.5 | 256.90 | 5762.3 | 22.4 | 267.25 | 6196.6 | 23.2 |
| 4.0 | 270.83 | 5491.2 | 20.3 | 286.79 | 6188.8 | 21.6 |
| 4.5 | 296.09 | 5586.8 | 18.9 | 376.95 | 6715.1 | 17.8 |
| 5.0 | 336.06 | 5678.7 | 16.9 | 440.85 | 6314.1 | 14.3 |
| 5.5 | 384.09 | 5560.5 | 14.5 | 506.29 | 6400.3 | 12.6 |
| 6.0 | 423.32 | 5629.8 | 13.3 | — | — | — |

Figure 15:
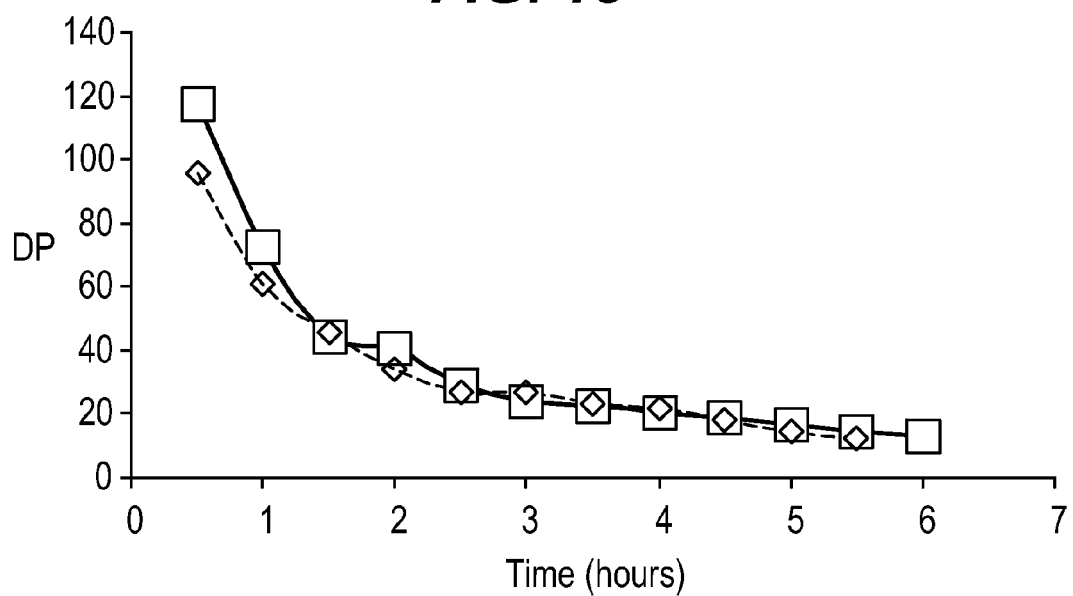
FIG. 15 shows the decrease in DP of MenW135 (□) and MenY (◇) during depolymerisation as measured by HPAEC-PAD.
Figure 16A:
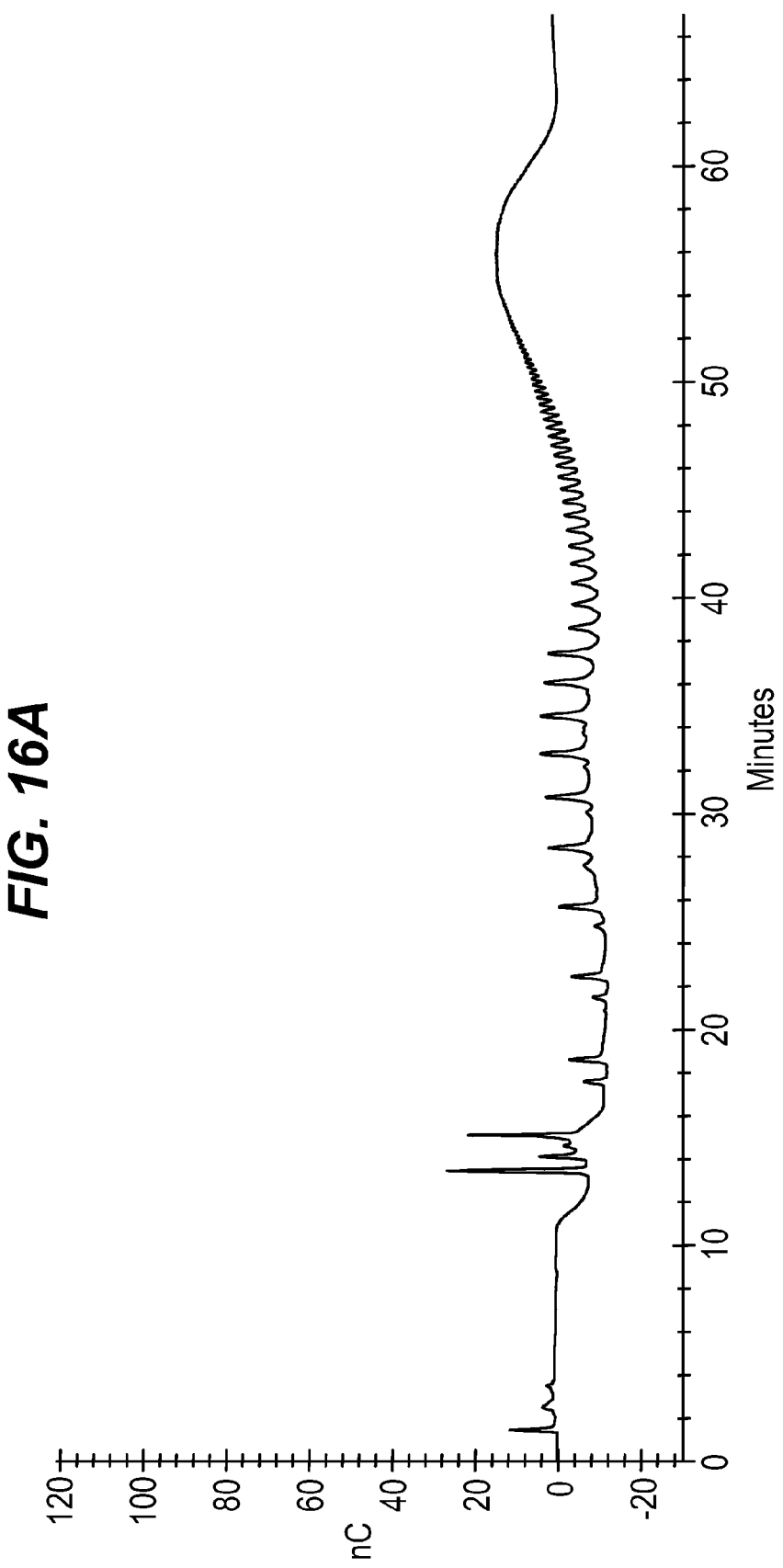
FIGS. 16 and 17 show the increase in short length oligos during the same process, for MenW135 (16) and MenY (17), comparing time zero (A) with final mixtures (B).
Figure 16B:
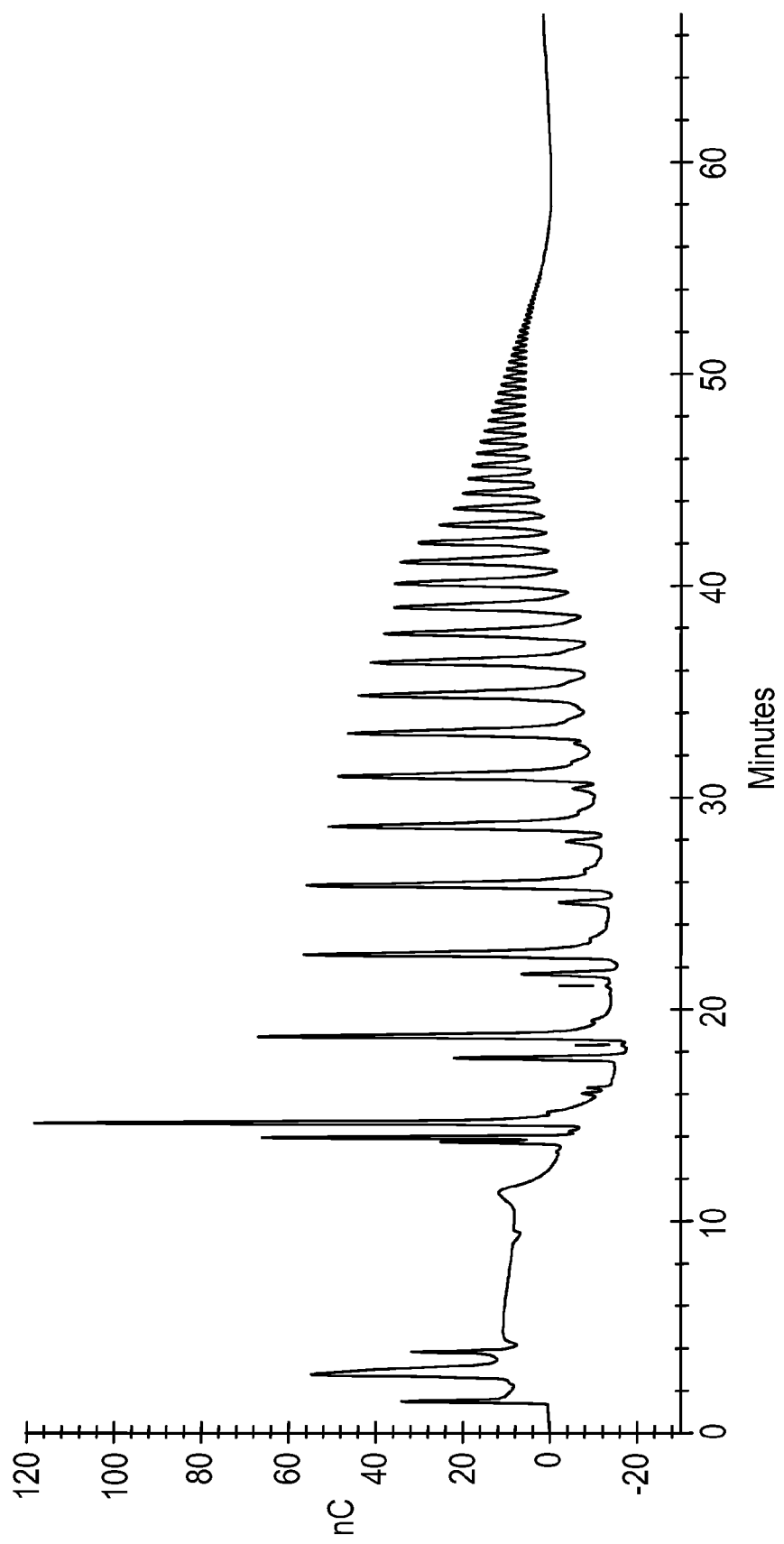
Figure 17A:
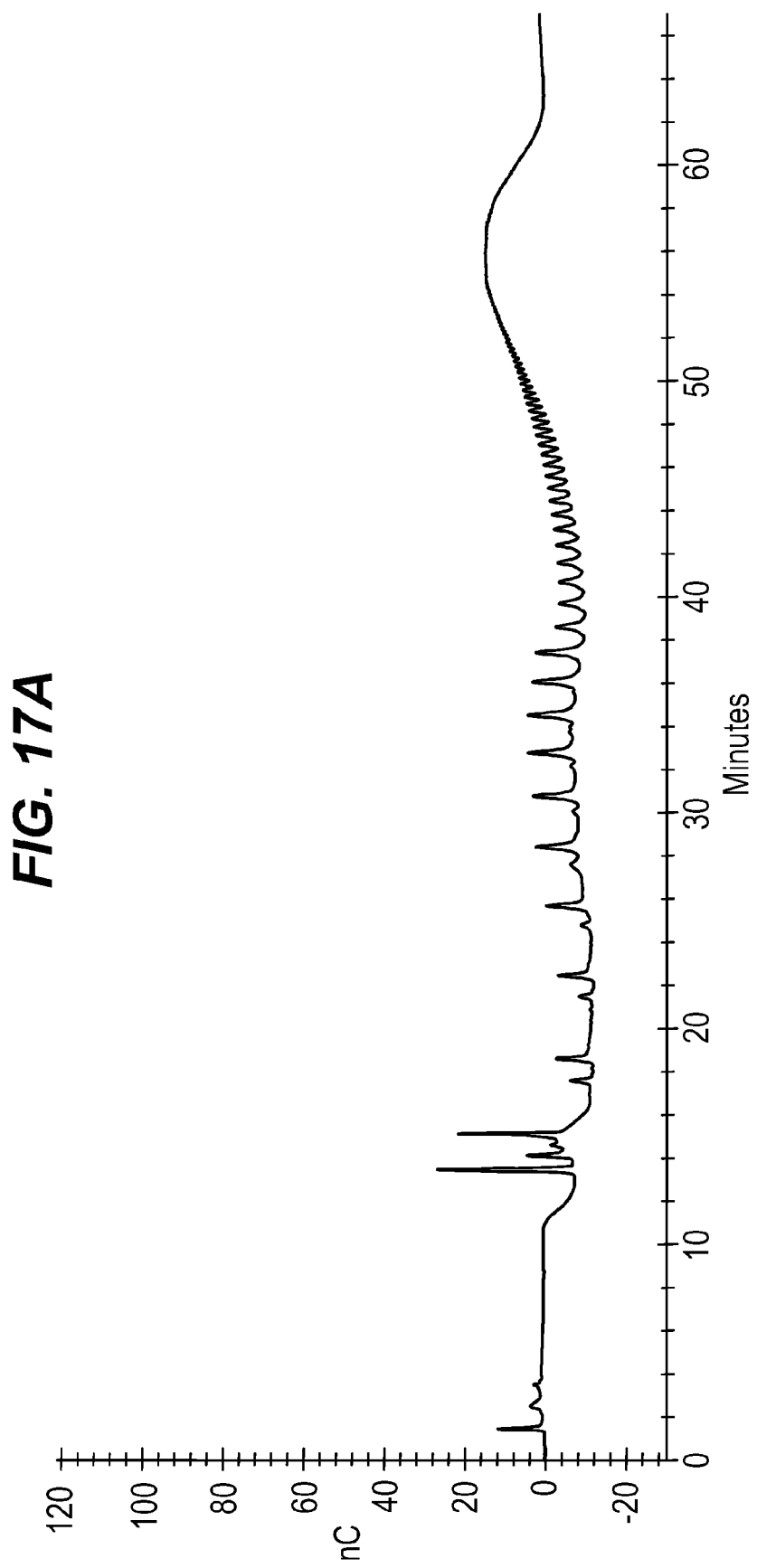
Figure 17B:
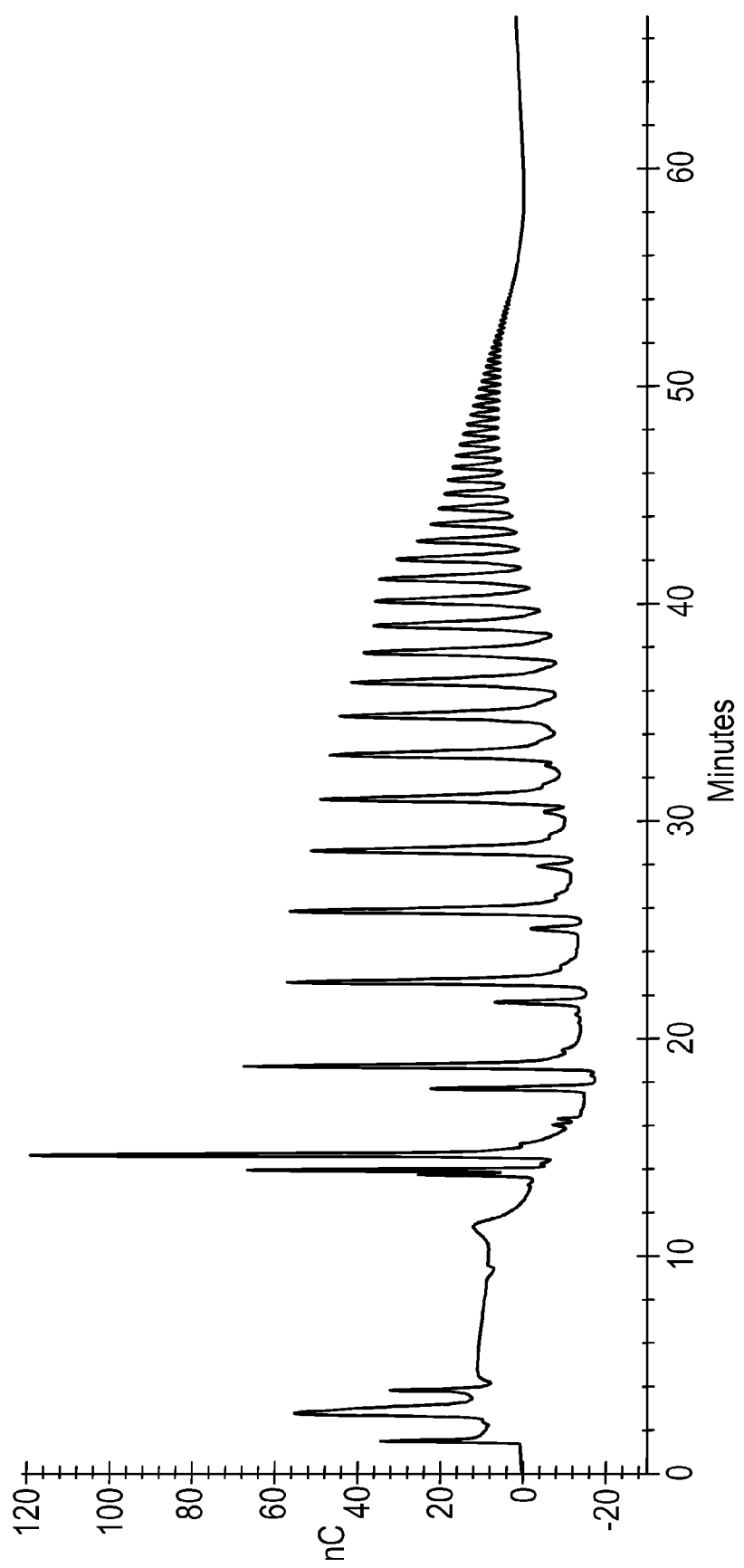

Thus the DP measurements show a gradual decrease in DP over time (FIG. 15). Confirmation of the depolymerisation was obtained with IonPac AS11 chromatographic analysis that shows how low molecular weight oligosaccharide content increases with time during acid hydrolysis, as shown in FIGS. 16 (MenW315) & 17 (MenY), where 16A/17A is time zero and 16B/17B is after 6 hours.

Serogroup W135 sample

Capsular saccharide from serogroup W135 was prepared. During preparation, its DP was measured using the methods disclosed herein. A chromatogram for a 100-fold dilution of this material is shown in FIG. 21B, with a 6 µg/ml standard being shown in FIG. 21A. Elution in both cases used 100 mM sodium acetate plus 20 mM NaOH, and is shown rising linearly from 10% elution buffer to 30% elution buffer over 30 minutes, with a final jump to 100% elution buffer for 10 minutes.

Sialitol in the standard was shown to elute at 16.383 minutes; in the sample there was a peak at 16.350 minutes.

Analysis characteristics from two separate analyses of the same sample, and five standard samples, are shown below, together with the calculated concentration of sialitol, were as follows:

| Sample Name | Retention Time (min) | Area (nC * min) | Height (nC) | Amount (µg/ml) |
|---|---|---|---|---|
| std1 | 16.700 | 0.8446 | 1.80 | 0.5023 |
| std2 | 16.584 | 1.6986 | 3.50 | 1.0103 |
| std3 | 16.134 | 3.4018 | 6.33 | 2.0234 |
| std4 | 16.567 | 6.8201 | 14.27 | 4.0566 |
| std5 | 16.384 | 10.0077 | 19.34 | 5.9526 |
| W135(a) | 16.350 | 5.4644 | 11.35 | 3.2502 |
| W135(b) | 16.600 | 5.7620 | 12.46 | 3.4272 |

Based on the mean of analyses (a) and (b), there was 3.339 µg/ml sialitol in the sample. Adjusting for the initial dilution, the original sialitol concentration was 333.9 µg/ml. Total sialic acid was measured as 5732.6 µg/ml, giving a DP value of 17.2.

Serogroup C analysis

Figure 18:
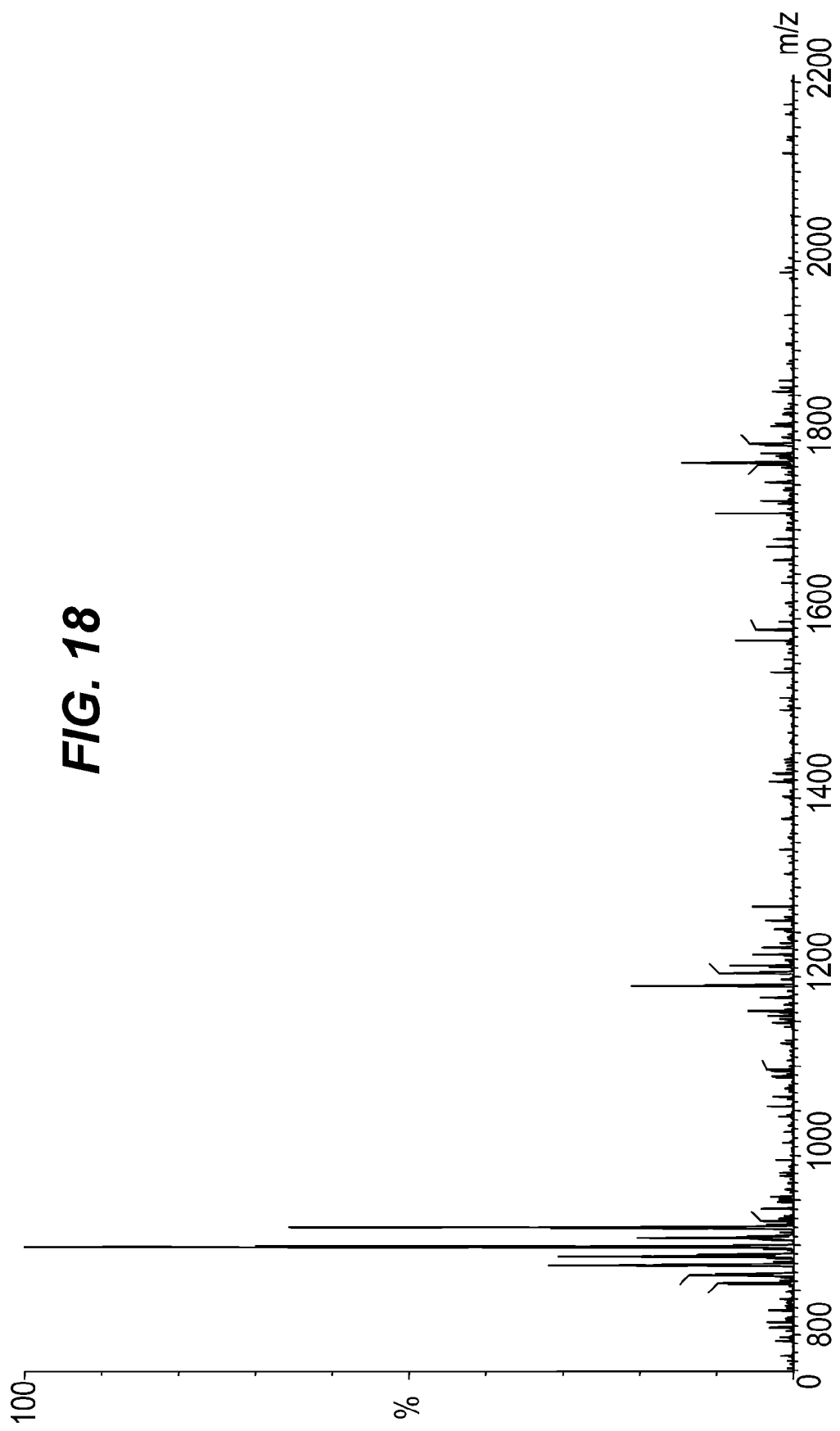
FIG. 18 shows an ESI spectrum of MenC DP5.

Purified MenC DP5 oligosaccharide was obtained as previously described [5]. ESI MS analysis was performed in the positive ion mode. The mass spectrum is shown in FIG. 18, where three main group of ions are evident. Detailed inspection of the peaks with the highest intensity (856-941 m/z) indicated that they correspond to doubly charged pentasaccharides while peaks ranging from 1733-1826 m/z correspond to single charged pentasaccharides, both differing for the number of O-acetyl substituents and of sodium as counter ions.

Figure 19:
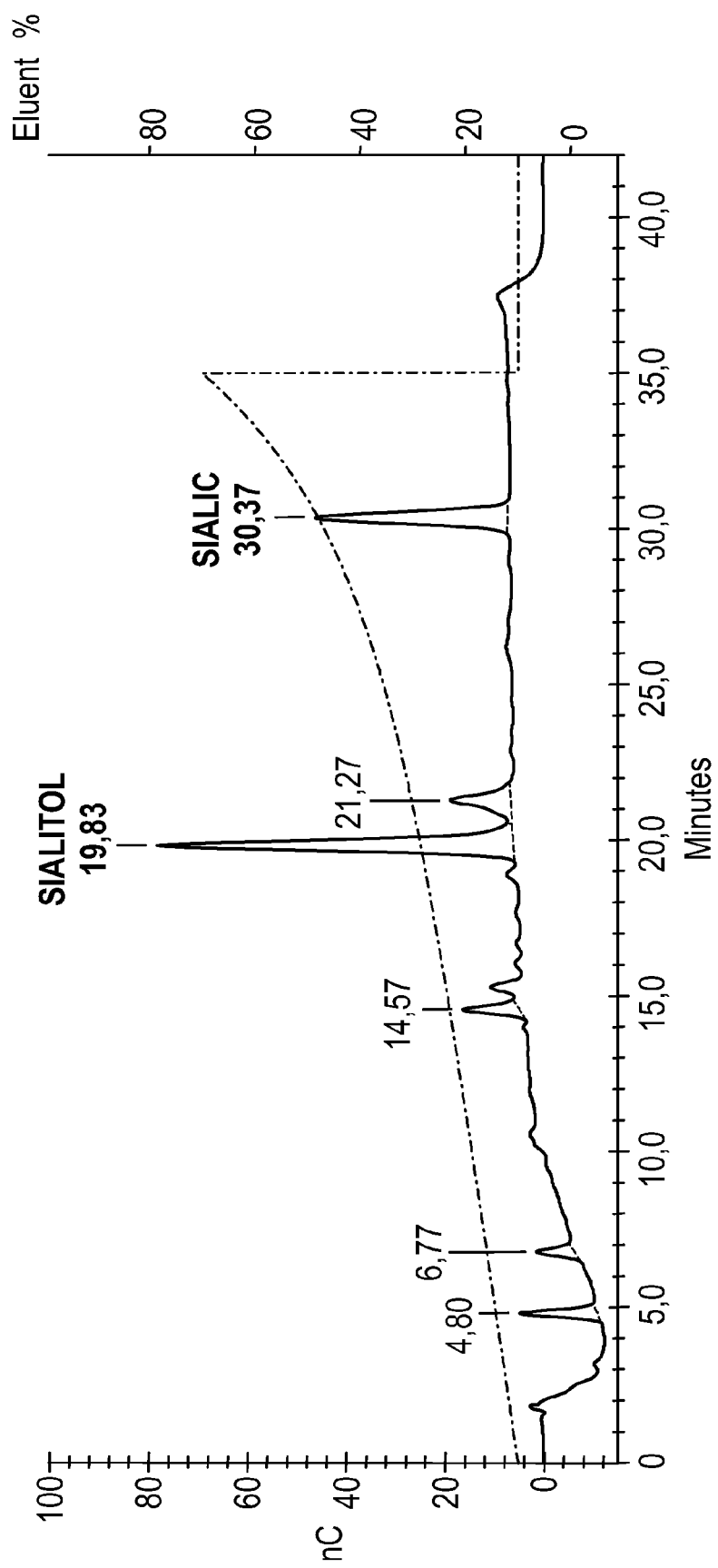
FIG. 19 shows HPAEC analysis of the same.

The DP of MenC DP5 oligosaccharides was determined with the chromatographic methods of the invention, and a chromatogram of the analysis is shown in FIG. 19. Four separate analyses of the oligosaccharides were prepared, and results were as follows:

| Sialitol (µg/ml) | Sialic acid (µg/ml) | DP | Average | Std Dev | CV % |
|---|---|---|---|---|---|
| 160.7 | 845.4 | 5.3 | 5.0 | 0.2 | 3.1 |
| 170.3 | 845.4 | 5.0 | | | |
| 169.1 | 845.4 | 5.0 | | | |
| 172.2 | 845.4 | 4.9 | | | |

Conclusions

The molecular size of saccharides has been an important issue in the design of previous conjugate vaccines [6,7], with intermediate chain-length oligosaccharides showing better immunogenicity. Preparation, isolation and characterisation of intermediate MenW135 and MenY oligosaccharides has been shown, with acid hydrolysis driving the initial depolymersiation. of the capsular polysaccharide [79]. The invention offers a new chromatographic method for determining the degree of polymerisation of these oligosaccharides, and the method shows good precision and accuracy, confirmed by NMR and ESI-MS analysis. Moreover, the method can be used also for determining DP of oligosaccharides from serogroup C.

Additional experimental details can be found in reference 85.

It will be understood that the invention has been described by way of example only and modifications may be made whilst remaining within the scope and spirit of the invention.

References (The Contents of which are Hereby Incorporated by Reference)

[1] *Vaccines* (eds. Plotkin et al.) 4th edition, ISBN: 0721696880.
[2] Baker et al. (2003) *J Infect Dis* 188:66-73.
[3] Theilacker et al. (2003) *Infect Immun* 71:3875-84.
[4] Anonymous (2003) *Drugs R D* 4:383-5.
[5] Ravenscroft et al. (1999) *Vaccine* 17:2802-2816.
[6] Paoletti et al. (1992) *J Clin Invest* 89:203-9.
[7] Anderson et al. (1986) *J Immunol* 137:1181-6.
[8] Jones (2001) *Curr Opin Investig Drugs* 2:47-49.
[9] Corbel (1996) *Dev Biol Stand* 87:113-124.
[10] WO03/080678.
[11] Costantino et al. (1999) *Vaccine* 17:1251-63.
[12] D'Ambra et al. (1997) *Anal Biochem* 250:228-36.
[13] Ravenscroft et al. (2000) *Dev Biol (Basel)* 103:35-47.
[14] Ashwell et al. (1994) *Anal Biochem* 222:495-502.
[15] WO2005/033148.
[16] Hallenbeck et al. (1987) *J Biol Chem* 262(8):3553-61
[17] Jumel et al. (2002) *Biotechnol Appl Biochem* 36:219-226.
[18] Hardy et al. (1988) *Anal Biochem* 170:54-62.
[19] Wang et al. (1990) *Anal Biochem* 190:182-187.
[20] Ramsay et al. (2001) *Lancet* 357(9251):195-196.
[21] Lindberg (1999) *Vaccine* 17 Suppl 2:S28-36.
[22] Buttery & Moxon (2000) *J R Coll Physicians Lond* 34:163-168.
[23] Ahmad & Chapnick (1999) *Infect Dis Clin North Am* 13:113-133, vii.
[24] Goldblatt (1998) *J. Med. Microbiol.* 47:563-567.
[25] European patent 0477508.
[26] U.S. Pat. No. 5,306,492.
[27] WO98/42721.
[28] *Conjugate Vaccines* (eds. Cruse et al.) ISBN 3805549326, particularly vol. 10:48-114.
[29] Hermanson (1996) *Bioconjugate Techniques* ISBN: 0123423368 or 012342335X.
[30] U.S. Pat. No. 4,761,283
[31] U.S. Pat. No. 4,356,170
[32] WO00/10599
[33] Geyer et al. Med. Microbiol. Immunol, 165: 171-288 (1979).
[34] U.S. Pat. No. 4,057,685.
[35] U.S. Pat. Nos. 4,673,574; 4,761,283; 4,808,700.
[36] U.S. Pat. No. 4,459,286.
[37] U.S. Pat. No. 4,965,338
[38] U.S. Pat. No. 4,663,160.
[39] Anonymous (January 2002) *Research Disclosure*, 453077.
[40] Anderson (1983) *Infect Immun* 39(1):233-238.
[41] Anderson et al. (1985) *J Clin Invest* 76(1):52-59.
[42] EP-A-0372501.
[43] EP-A-0378881.
[44] EP-A-0427347.
[45] WO93/17712
[46] WO94/03208.
[47] WO98/58668.
[48] EP-A-0471177.
[49] WO91/01146
[50] Falugi et al. (2001) *Eur J Immunol* 31:3816-3824.
[51] EP-A-0594610.
[52] WO00/56360.
[53] WO02/091998.
[54] WO01/72337
[55] WO00/61761.
[56] WO99/42130
[57] WO96/40242
[58] PCT/IB2005/000987.
[59] WO02/09643.
[60] Katial et al. (2002) *Infect Immun* 70:702-707.
[61] WO01/52885.
[62] European patent 0301992.
[63] Bjune et al. (1991) *Lancet* 338(8775):1093-1096.
[64] Fukasawa et al. (1999) *Vaccine* 17:2951-2958.
[65] WO02/09746.
[66] Rosenqvist et al. (1998) *Dev. Biol. Stand.* 92:323-333.
[67] Watson (2000) *Pediatr Infect Dis J* 19:331-332.
[68] Rubin (2000) *Pediatr Clin North Am* 47:269-285, v.
[69] Jedrzejas (2001) *Microbiol Mol Biol Rev* 65:187-207.
[70] Bell (2000) *Pediatr Infect Dis J* 19:1187-1188.
[71] Iwarson (1995) *APMIS* 103:321-326.
[72] Gerlich et al. (1990) *Vaccine* 8 Suppl: S63-68 & 79-80.
[73] Gustafsson et al. (1996) *N. Engl. J. Med.* 334:349-355.
[74] Rappuoli et al. (1991) *TIBTECH* 9:232-238.
[75] *Vaccines* (1988) eds. Plotkin & Mortimer. ISBN 0-7216-1946-0.
[76] Del Guidice et al. (1998) *Molecular Aspects of Medicine* 19:1-70.
[77] Sutter et al. (2000) *Pediatr Clin North Am* 47:287-308.
[78] Zimmerman & Spann (1999) *Am Fam Physician* 59:113-118, 125-126.
[79] WO03/007985.
[80] Svennerholm (1957) *Biochem Biophys Acta* 24:604-11.
[81] Lernercinier & Jones (1996) *Carbohydr Res* 296:83-96.
[82] Ip et al. (1992) *Anal Biochem* 201:343-349.
[83] Neeser & Schweizer (1984) *Anal Biochem* 142:58-67.
[84] Bierman. *Hydrolysis and other cleavages of glycosidic bonds*. In: *Analysis of Carbohydrates by GLC and MS* (Eds Bierman & McGinnis) CRC Press Inc., Boca Raton, Fla., 1989, pp. 27-41.
[85] Bardotti et al. (2005) *Vaccine* 23:1887-99.

We claim:

1. A method for preparing a vaccine composition, comprising the steps of:
   (a) providing a capsular saccharide whose degree of polymerization (DP) has been measured by a process comprising the steps of:
      (i) reducing the terminal sialic acid monosaccharide subunit to give a reduced sialic acid monosaccharide subunit;
      (ii) hydrolyzing the saccharide to give a hydrolysate containing monosaccharide subunits, wherein the hydrolysis proceeds to completion to yield only monosaccharide subunits; and
      (iii) determining the ratio of total sialic acid to reduced sialic acid in the hydrolysate,
      wherein the capsular saccharide comprises sialic acid monosaccharide subunits that are linked α 2→9 and has a terminal sialic acid monosaccharide subunit;
   (b) conjugating the DP-analyzed capsular saccharide to one or more carrier proteins;
   (c) analyzing the bulk vaccine comprising the conjugated capsular saccharide for pH and/or other properties; and, if the results from step (c) indicate that the bulk vaccine is acceptable for clinical use,
   (d) preparing and packaging the vaccine for human use from the bulk vaccine.

2. The method of claim 1, wherein the terminal sialic acid residue is reduced by incubating the saccharide with a reducing agent.

3. The method of claim 2, wherein the reducing agent is sodium borohydride.

4. The method of claim 1, wherein acid hydrolysis is used.

5. The method of claim 2, wherein acid hydrolysis is used.

6. The method of claim 3, wherein acid hydrolysis is used.

7. The method of claim 1, where the capsular saccharide is a population of different-sized capsular saccharides, and the process provides the average degree of polymerization of the capsular saccharides.

8. The method of claim 2, where the capsular saccharide is a population of different-sized capsular saccharides, and the process provides the average degree of polymerization of the capsular saccharides.

9. The method of claim 3, where the capsular saccharide is a population of different-sized capsular saccharides, and the process provides the average degree of polymerization of the capsular saccharides.

10. The method of claim 4, where the capsular saccharide is a population of different-sized capsular saccharides, and the process provides the average degree of polymerization of the capsular saccharides.

11. The method of claim 7, where the capsular saccharide is a population of different-sized capsular saccharides, and the process provides the average degree of polymerization of the capsular saccharides.

12. The method of claim 1 wherein step (ii) of the process further comprises starting depolymerization of the capsular saccharide; and, at one or more time points thereafter prior to complete hydrolysis, measuring DP of the capsular saccharide by determining the ratio of total sialic acid to reduced sialic acid in the hydrolysate.

13. The method of claim 2 wherein step (ii) of the process further comprises starting depolymerization of the capsular saccharide; and, at one or more time points thereafter prior to complete hydrolysis, measuring DP of the capsular saccharide by determining the ratio of total sialic acid to reduced sialic acid in the hydrolysate.

14. The method of claim 3 wherein step (ii) of the process further comprises starting depolymerization of the capsular saccharide; and, at one or more time points thereafter prior to complete hydrolysis, measuring DP of the capsular saccharide by determining the ratio of total sialic acid to reduced sialic acid in the hydrolysate.

15. The method of claim 10 wherein step (ii) of the process further comprises starting depolymerization of the capsular saccharide; and, at one or more time points thereafter prior to complete hydrolysis, measuring DP of the capsular saccharide by determining the ratio of total sialic acid to reduced sialic acid in the hydrolysate.

16. The method of claim 11 wherein step (ii) of the process further comprises starting depolymerization of the capsular saccharide; and, at one or more time points thereafter prior to complete hydrolysis, measuring DP of the capsular saccharide by determining the ratio of total sialic acid to reduced sialic acid in the hydrolysate.

17. The method of claim 1 wherein the capsular saccharide is from meningococcal serogroup W135 or serogroup Y.

18. The method of claim 3 wherein the capsular saccharide is from meningococcal serogroup W135 or serogroup Y.

19. The method of claim 7 wherein the capsular saccharide is from meningococcal serogroup W135 or serogroup Y.

* * * * *